(12) United States Patent
Maiti et al.

(10) Patent No.: US 6,930,182 B1
(45) Date of Patent: Aug. 16, 2005

(54) **COMPOSITION AND METHODS OF USING THE *MIRABILIS MOSAIC* CAULIMOVIRUS SUB-GENOMIC TRANSCRIPT (SGT) PROMOTER FOR PLANT GENETIC ENGINEERING**

(75) Inventors: Indu B. Maiti, Lexington, KY (US); Nrisingha Dey, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 284 days.

(21) Appl. No.: 10/161,718

(22) Filed: Jun. 5, 2002

Related U.S. Application Data

(60) Provisional application No. 60/295,566, filed on Jun. 5, 2001.

(51) Int. Cl.$^7$ .................. C07H 21/04; C12N 15/00; C12N 15/09; C12N 15/70; C12N 5/04
(52) U.S. Cl. ................ 536/24.1; 435/320.1; 435/419; 536/23.1
(58) Field of Search ............... 536/24.1, 23.1; 435/320.1, 419

Primary Examiner—James Ketter
Assistant Examiner—Konstantina Katcheves
(74) Attorney, Agent, or Firm—McDermott Will & Emery LLP

(57) ABSTRACT

The isolation of and methods of using a sub-genomic transcript (Sgt) promoter from *Mirabilis mosaic* virus (MMV) are described. A 333 bp MMV Sgt promoter fragment (sequence−306 to +27 from the transcription start site, TSS) was found to be sufficient for strongest promoter activity. This MMV Sgt promoter fragment shows comparable promoter activity to the MMV FLt promoter both in transgenic plants and in protoplasts. The MMV Sgt promoter also demonstrates much greater activity compared to *Cauliflower mosaic* virus (CaMV) 19S promoter and 35S promoter. The MMV Sgt promoter fragment and any chimeric gene to which it may be linked are usefull for plant geneic engineering to obtain transgenic plants, plant cells and seeds.

32 Claims, 8 Drawing Sheets

Figure 1

Figure 2:
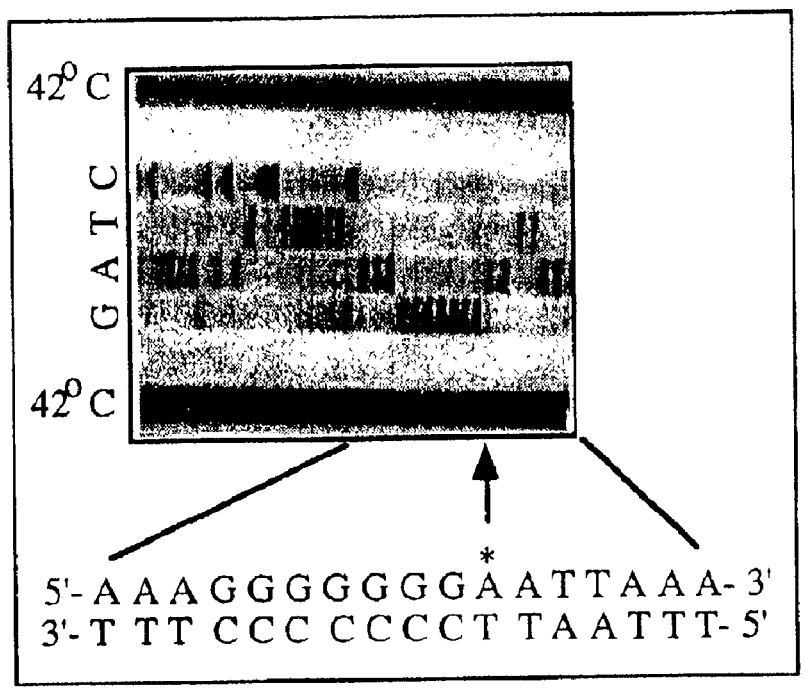

```
     -646                                                -606
       ↓                                                   ↓
     GAAAAACGGA AACCGTTACA GGTAAAGTTG AAGAAAGATC AGGTATGGAT CTGGACGCAA   -587
                                   -556
                                     ↓
     TCAGATACTG ATTACGTTAA AAAGATAAAG AAAGGATTAA TTAATTTTCC AAAACTTTAT   -527
                      -506
                        ↓
     CTACCAAAGA AAGAAGACAG TTTAATTATT GAAACTGATG CTTCTGATCA CTTTTGGGGT   -467
               -456
                 ↓
     GGAGTCCTTA AGGCCCAAAC CACTGAAGGT GAAGAATTAA TCTGCAGGTA TTCTTCAGGA   -407
     -406                                                -356
       ↓                                                   ↓
     ACATTCAAAC CAGCAGAATT GAATTACCAT AGTAATGAGA AAGAATTACT AGCGGTAAAA   -347
                                             -306
                                               ↓
     CAGGTGATTA CTAAATTTAG TATTTATCTA ACCCCTGTTT GTTTACAGT CAGGACAGAT    -287
                                -256
                                  ↓
     AATGTAAATC TTTTAAAAGG ATTTATGAAT AAAAAGATTA CTGGTGACAG TAAACAGGGA   -227
                   -206
                     ↓
     AGGCTAATAA GATGGCAAAT GTGGTTTTCA CATTACACCT TAAGGTGGA CCACCTAAAA    -167
            -156                                -117
              ↓                                   ↓
     GGAGAACAAA ATGTGCTGGC TGATTATCTC ACCAGAGaat tacccgggcA ATTCCACAAT   -107
                -94         -74
                 ↓           ↓
     GGAAACGTCA TCCATGACGA CTAAACCTGC CATTTTTCGG CTATAAAAAC TGGGTTTTTC   -47
         -44                            ↑                TSS (+1)
          ↓                            -74                 |
     CAAATGAAAA TTCCACACAA AACACATCCT TTTTTCAAAG GGGGGGAATT AAATCAAAAA   +14
                        ↑
              ↓        -19
     CAGGAAAAAC AAAAACCAGT AATGGAAAAA GAGCTTCAGG CTCTAAGGAT CAAAGAAAAG  +74
          ↑                                 ↑
         +27                               +50
     ATCCTCTTGG TAGAACTCGA TTCTATCAGAA AACAAATCAG CATTTACGCT GAACTAACTG  +135
       ↑                                                 ↑
      +77                                              +127
     GAAGTTTAGA CCAGGAAGGC TCTGCCTCAC ACTCTAAACC TAGTCCACAG CAAACGGCTG   +195
                                           ↑
                                         +177
     ATGGTAAAGA CGGCTCAAAT CCGTTAAACC CTGATGCTTT GGGAAAAAGC ATAACGGAGA   +255
                                   ↑
                                 +228
     ACTTGGTTCC AAGTCCTGAG AAGGATGAAT CCAAGAAAGT TGTCAGTTTA CGAAAAACTG   +315
             ↑
           +277
     AAAGTGGGTT GTATATCCCC ACGACTAGTC CGGTTGCAAA CGGCTCCGGT AAAGACACAA CAA+378
       ↑                                                              ↑
     +328                                                           +378
```

Figure 3, A and B
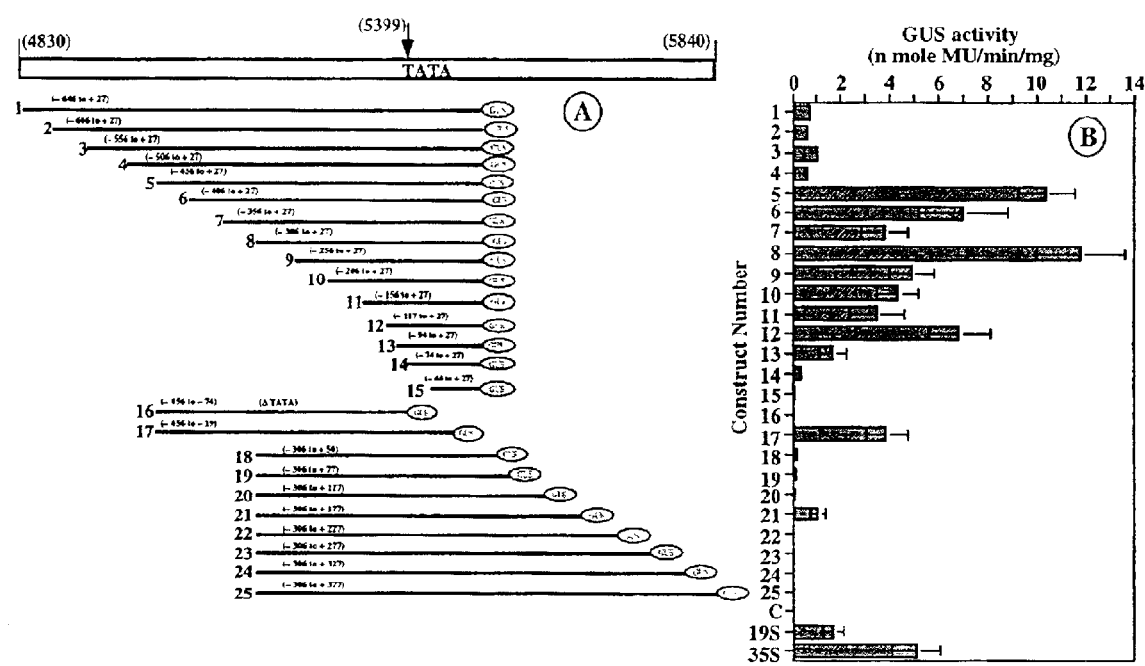

Figure 5 A and B
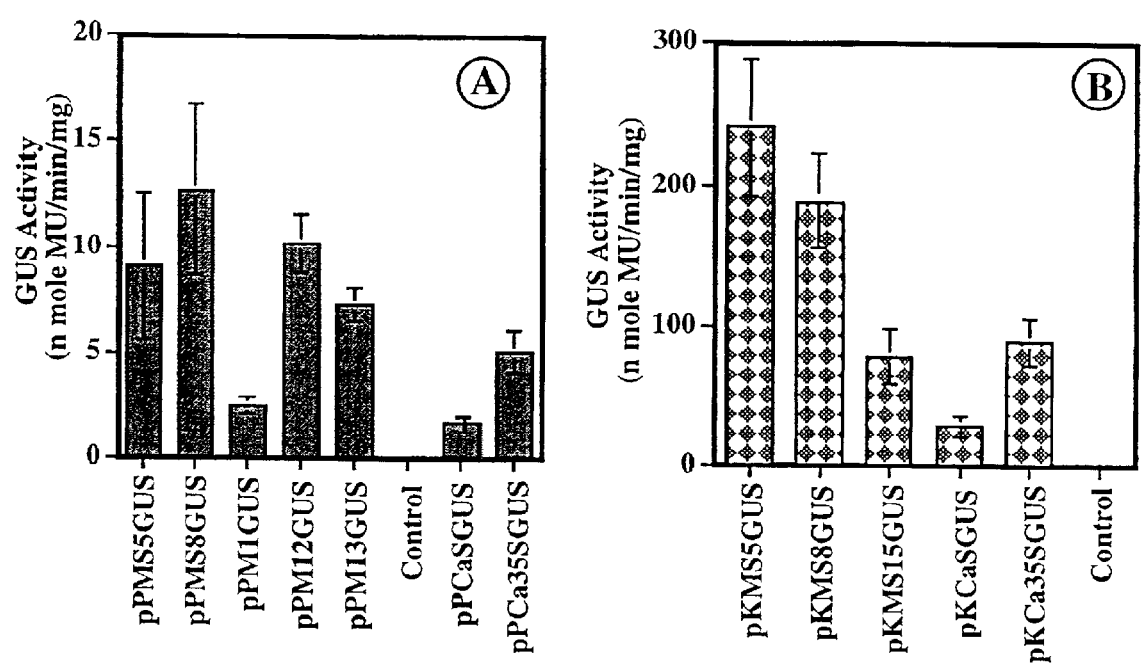

COMPOSITION AND METHODS OF USING THE *MIRABILIS MOSAIC* CAULIMOVIRUS SUB-GENOMIC TRANSCRIPT (SGT) PROMOTER FOR PLANT GENETIC ENGINEERING

This application claims priority to U.S. application Ser. No. 60/295,566, filed Jun. 5, 2001.

FIELD OF THE INVENTION

This invention relates generally to plant genetic engineering and plant molecular biology. More particularly, the invention relates to the isolation and use of a new plant promoter for driving the expression of plant genes.

BACKGROUND OF THE INVENTION

The *Mirabilis mosaic* virus (MMV) infects *Mirabilis* plant species (family *Nyctaginaceae*), a member of the *Caulimoviridae* family. The virus has a circular double-stranded DNA genome of about 8 Kb with four single-stranded discontinuities in the DNA, one in the alpha strand and three in the complementary strand [1]. The restriction map of the MMV genome is quite different from that of the other members of the genus *Caulimovirus* [1]. The MMV virus was characterized as a member of the genus *Caulimovirus* based upon the morphology of its virions and inclusion bodies [2].

Recently, MMV has been fully sequenced, and homology analysis of its genomic DNA has shown that it is a definitive member of the genus *Caulimovirus* [Maiti, unpublished]. However, MMV is serologically distinct from the *Cauliflower mosaic* virus (CaMV), the type species of this genus [2].

Several *Caulimoviridae* genomes have been fully sequenced and characterized. These include *Cauliflower mosaic* virus (CaMV) [3], *Carnation etched ring* virus (CERY) [4], *Figwort mosaic* virus (FMV) [5], *Soybean chlorotic mottle* virus (SoCMV) [6], *Peanut chlorotic streak* virus (PCISV) [7], *Casava vein mosaic* virus (CVMV) [8], *Strawberry vein banding* virus (SVBV) [9], *Petunia vein clearing virus* PVCV) [10], and *Mirabilis mosaic* virus (MMV) [Maiti, unpublished].

The *Caulimovirus* genome generally contains two transcriptional promoters, one for the full-length transcript and the other for the subgenomic transcript. These transcripts are equivalent to the CaMV 35S and 19S transcript respectively [6, 11, 12]. A number of strong constitutive promoters have been derived from viruses of the *Caulimoviridae* family, particularly from the *Cauliflower mosaic* virus (CaMV): CaMV35S and 19S promoter[13, 14]. Genetic promoters have also been isolated from other members of this family, namely *Rice tungro* bacilliform virus RTBV) [15], *Commelina yellow* mottle virus (CYMV) [16], *Soybean chlorotic mottle* virus (SoCMV) [6], *Figwort mosaic* virus (FMV, strain DxS) [17, 18]), FMV strain M3 [19], *Cassava vein mosaic* virus (CVMV) [20], *Peanut cholotic* streak virus (PCISV) [21] and *Mirabilis mosaic* virus (MMV) [22, 23] and used for the construction of plant transformation vectors. Transcript promoters from *Caulimoviruses,* such as CaMV, FMV, PCISV, MMV and FMV are active in all plant organs [13, 18, 21–23], whereas, transcript promoters from *Badnaviruses,* such as CYMV and RTBV are phloem-specific [15, 16] in expressing genes in transgenic plants.

The CaMV 35S promoter has been well characterized [13, 24–30] and widely used in chimeric gene constructs for heterologous gene expression in transgenic plants [31–33]. The CaMV 35S promoter is also active in bacteria [34], yeast [35], Hela cells [36] and *Xenopus oocytes* [37].

The expression of useful foreign traits in plants is a major focus in plant biotechnology. There is a need for a variety of different (e.g., constitutive, tissue specific and/or inducible) promoters that meet the different potential applications in this field of plant genetic engineering. Introduction of heterologous genes of interest into plant cells generates the desired qualities in the plants of choice (Maiti and Hunt, 1992; Wagner, 1992). Plant biotechnology is leading a rapid progress in production of economically valuable germplasm with improved characteristics or traits such as insect resistance, virus resistance, fungal resistance, herbicide resistance, bacterial or nematode pathogen resistance, cold or drought tolerance, improved nutritional value, seed oil modification, delayed ripening of fruits, and male sterility, to name a few. These germplasms provide an enhanced development in breeding programs for crop improvement as well as a better understanding of gene regulation and organization in transgenic plants.

Plant metabolic engineering is the application of genetic engineering methods to modify the nature of chemical metabolites in plants. For metabolic engineering where multiple genes need to be inserted into a single cell, the use of different strong constitutive promoters is desirable in order to avoid genetic instability caused by recombination between identical or closely related promoter sequences, for example, those taken from plants themselves. Through use of these promoter sequences the introduced genes can be transcribed to messenger RNA and then translated to resultant proteins to exhibit new traits or characters.

Besides developing useful traits in crops, plant molecular engineering will lead to further understanding of molecular pathways involved in disease development and secondary metabolism in plants. Moreover, by engineering plants with specific foreign genes, the responses of plants to abiotic and biotic stress and stress related metabolism can be analyzed.

Thus, there is a need in the art for plant promoters that can be used to drive the expression of genetically engineered genes in plants.

SUMMARY OF THE INVENTION

In one aspect of the invention there is provided an isolated DNA molecule comprising a *mirabilis mosaic* virus (MMV) subgenomic transcript (Sgt) promoter comprising the nucleotide sequence of SEQ ID NO:1 or a fragment thereof having at least about 30% MMV Sgt promoter activity. In a preferred embodiment of this aspect of the invention the Sgt promoter is a fragment comprising the nucleotide sequence of −306 to +27 of SEQ ID NO:1. In another preferred embodiment, the MMV Sgt promoter is a fragment comprising the nucleotide sequence of −456 to +27 of SEQ ID NO:1. In a most preferred embodiment, the MMV Sgt promoter of the invention is operably linked to a nucleotide sequence which encodes a polypeptide. In yet another preferred embodiment, the MMv Sgt promoter has the nucleotide sequence of SEQ ID NO:2.

In another aspect of the invention, there is provided an intermediate plant transformation plasmid comprising a region of homology to an *Agrobacterium tumefaciens* gene vector, an *Agrobacterium tumefaciens* T-DNA border region and a chimeric gene located between the T-DNA border and the region of homology, said chimeric gene comprising a MMV Sgt promoter comprising MMV Sgt promoter comprising the nucleotide sequence of SEQ ID NO:1 or a fragment thereof having at least about 30% MMV Sgt promoter activity, wherein the MMV Sgt promoter or fragment thereof is operably linked to a nucleotide sequence encoding a polypeptide. In a preferred embodiment of this aspect of the invention, the chimeric gene further comprises a MMV leader sequence operably linked to said nucleotide sequence. In another preferred embodiment of this aspect of the invention the MMV Sgt promoter comprises at least one enhancer domain.

In yet another aspect of the invention, there is provided a plant transformation vector comprising a disarmed *Agrobacterium tumefaciens* plant tumor-inducing plasmid and a chimeric gene, said chimeric gene comprising a MMV Sgt promoter comprising the nucleotide sequence of SEQ ID NO:1 or a fragment thereof having at least about 30% MMV Sgt promoter activity, wherein the MMv Sgt Promoter or fragment thereof is operably linked to a nucleotide sequence encoding a polypeptide. In a preferred embodiment of this aspect of the invention, the MMV Promoter comprises at least one enhancer domain.

In another aspect of the invention, there is provided an intermediate plant transformation plasmid comprising a region of homology to an *Agrobacterium tumefaciens* gene vector, an *Agrobacterium tumefaciens* T-DNA border region and a chimeric gene located between the T-DNA border and the region of homology, said chimeric gene comprising a MMV Sgt promoter comprising the nucleotide sequence of SEQ ID NO:1 or a fragment thereof having at least about 30% MMV Sgt promoter activity, wherein the MMV Sgt promoter or fragment thereof is operably linked to a nucleotide sequence encoding a polypeptide.

In a further aspect of the invention, there is provided a transgenic plant or transgenic plant part comprising a plant transformation vector comprising a disarmed *Agrobacterium tumefaciens* plant tumor-inducing plasmid and a chimeric gene, said chimeric gene comprising a MMV Sgt promoter comprising the nucleotide sequence of SEQ ID NO:1 or a fragment thereof having at least about 30% MMV Sgt promoter activity, wherein said MMV Sgt promoter or fragment thereof is operably linked to a nucleotide sequence which encodes a polypeptide; and wherein said chimeric gene is expressed in the plant. In a preferred embodiment of this aspect of the invention, the chimeric gene encodes a plant metabolic polypeptide or a polypeptide that confers pathogen resistance to the transgenic plant. In another preferred embodiment, the plant part is selected from the group consisting of a root, leaf, stem, flower petal, pollen, callus and cell.

In another aspect of the invention, there is a transformed plant protoplast comprising a plant transformation vector comprising a disarmed *Agrobacterium tumefaciens* plant tumor-inducing plasmid and a chimeric gene, said chimeric gene comprising a MMV Sgt promoter comprising the nucleotide sequence of SEQ ID NO:1 or a fragment thereof having at least about 30% MMV Sgt promoter activity, wherein said MMV Sgt promoter or fragment thereof is operably linked to a nucleotide sequence which encodes a polypeptide.

In yet another aspect of the invention, there is provided a method of making a transgenic plant comprising (1) transforming a plant cell with a chimeric gene comprising a MMV Sgt promoter comprising the nucleotide sequence of SEQ ID NO:1 or a fragment thereof having at least about 30% MMV Sgt promoter activity, wherein said MMV Sgt promoter or fragment thereof is operably linked to a nucleotide sequence which encodes a polypeptide; (2) culturing the plant cell under growing conditions to produce a regenerated plant; and (3) and expressing the chimeric gene in the regenerated plant.

There is also provided a promoter enhancer element having the sequence set forth in SEQ ID NO: 10.

BRIEF DESCRIPTION OF THE DRAWINGS

FIG. 1 shows the DNA sequence of the subgenomic transcript promoter from *mirabilis mosaic* virus (MMV) (SEQ ID NO:1). The nucleotide sequence of the MMV Sgt promoter (coordinates −646 to +377 in respect of transcription start site; corresponding coordinates in MMV genome 4829 to 5840), and a 1023 bp fragment including the 3' end of gene V, followed by the small intergenic region and 5' portion of gene VI presented from left to right in the 5' to 3' direction of the transcript. Modification of the promoter sequence resulted from insertion of an 'EcoRI to SmaI' adapter is shown in lower case. The end points for the 5' or the 3' deletion constructs are also indicated above or below the sequence, respectively. The TATA-box, (TATAA), CAT box (CAAT) and initiator ATG codon for gene VI are shown in bold. The transcriptional start site (TSS) is indicated as +1.

FIG. 2 is an autoradiograph showing the location of the transcriptional start site (TSS) of the MMV Sgt promoter by primer extension analysis. Primer extension was carried out as described in Example 4. Primer extension reaction products were subjected to electrophoresis on denaturing polyacrylamide gel containing urea, alongside with the sequence reaction of GUS gene construct (lane G, A, T and C). The process was performed with the same labeled primer. The minus strand DNA sequence read on the gel is shown, and the transcriptional start site (A*) in the corresponding plus strand is indicated by an arrow.

FIGS. 3A and 3B: FIG. 3A is a schematic map of the GUS constructs (number 1 to 25) developed for deletion analysis of the MMV Sgt promoter. The coordinates of the relative deletion fragments are given in parenthesis. The end points for the 5' or the 3' deletion constructs are also indicated above or below the sequence, respectively in FIG. 1. At the top, the relative position of the TATA box and the MMV genomic coordinates are shown. FIG. 3B is a bar graph showing MMV Sgt promoter expression analysis in a protoplast transient expression assay using a GUS reporter gene. Soluble protein extracts (5 $\mu$g) from transformed protoplasts were used for the GUS assay. Each construct was assayed at least three times in three independent experiments. The average GUS activity is presented in the histogram. Error bars show a 95% confidence interval of the means. The statistical (one-way analysis of variance, ANOVA) analysis showed an extremely significant P value of <0.001. C., untransformed control, extract from untransformed protoplast; 19S, 35S, GUS gene is directed by the CaMV 19S and 35S promoter, respectively.

FIGS. 4A and B: FIG. 4A is an autoradiograph of RNA dot-blot analysis of total RNA (10 $\mu$g) obtained from transformed protoplasts with construct No 1 to 25 as indicated in FIG. 3A. FIG. 4B is a Northern blot analysis of total RNA (10 $\mu$g) obtained from pPMS8GUS with 32P labeled GUS as probe (lane 2) and RNA obtained from untransformed Samsun NN plant (lane 1).

FIGS. 5A and B: FIGS. 5A and 5B are a bar graphs showing comparative expression analyses of the MMV Sgt promoter with the MMV FLt promoters and CaMV promoters (35S and 19S) in (A) transient expression in protoplasts and (B) stable expression in transgenic plants.

(5A): GUS constructs: pPMS5GUS, pPMS8GUS with the MMV Sgt promoter; pPM1GUS, pPM12GUS and pPM13GUS with MMV FLt promoter, as described earlier [22]; and pPCaSGUS and pPCa35SGUS with CaMV 19S and 35S promoters, respectively, were assayed in protoplast transient expression experiments. Each construct was assayed at least three times in three independent experiments. The average GUS activity is presented in the histogram. Error bars show a 95% confidence interval on the means. The statistical ANOVA analysis showed a P value <0.001; this is considered to be extremely significant.

(5B): The MMV Sgt promoter (GUS-constructs pKMS5GUS, pKM8GUS and pKMS17GUS) and CaMV 19 S and 35S promoter (GUS constructs pKCaSGUS and pKCa35SGUS respectively) were compared. The promoter activity was measured in four-week-old seedlings (R1 progeny) grown aseptically on an MS-agar medium in the presence of kanamycin (200 mg/ liter) and 3% sucrose. Soluble protein extract from the whole seedlings were used for the GUS assay. The data are means of five independent experiments for each construct; eight to ten independent transgenic lines developed for each construct were assayed. The average GUS activity is presented for each construct in the histogram, with standard deviation from the mean indicated by an error bar. Error bars show a 95% confidence interval on the means. The statistical ANOVA analysis indicated that the P value <0.001 means extremely significant. Untransformed control (Control), tissue extract from wild-type N. tabacum cv. SamsunNN.

Figure 6:
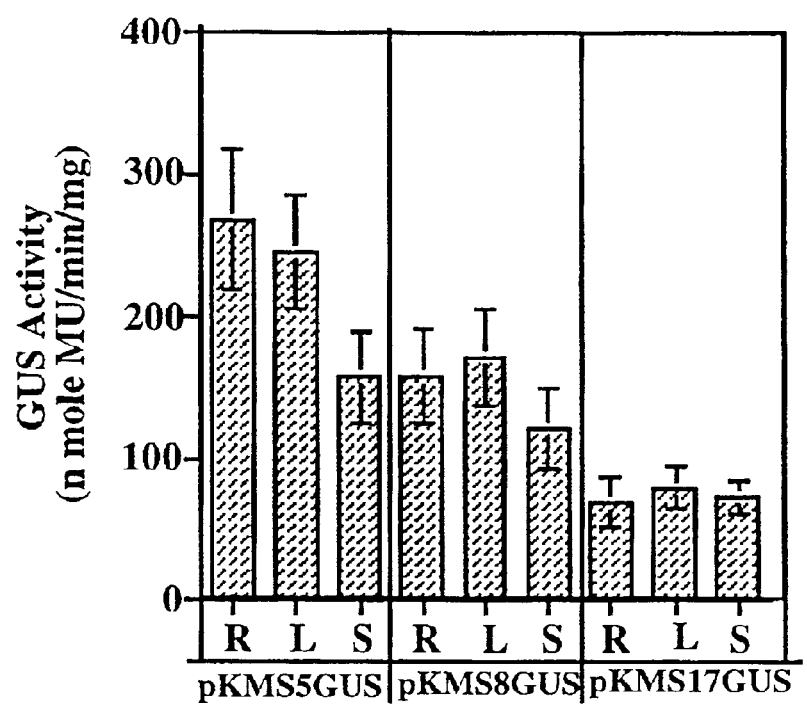

FIG. 6 is a histogram showing expression of MMV Sgt promoters in various parts (roots, R; leaves, L; stems, S) of four-week-old seedlings developed for pKMS5GUS, pKMS8GUS and pKMS17GUS. GUS activity was measured fluorometrically using soluble protein extract (5 μg) from roots, stems and leaves of seedlings. The presented value in the histogram, with standard deviation indicated by an error bar, is the average of six samplings from each of the eight independent lines developed for each construct. Error bar shows a 95% confidence interval on the means. The statistical ANOVA analysis showed that a P value <0.001 means extremely significant.

Figure 7:
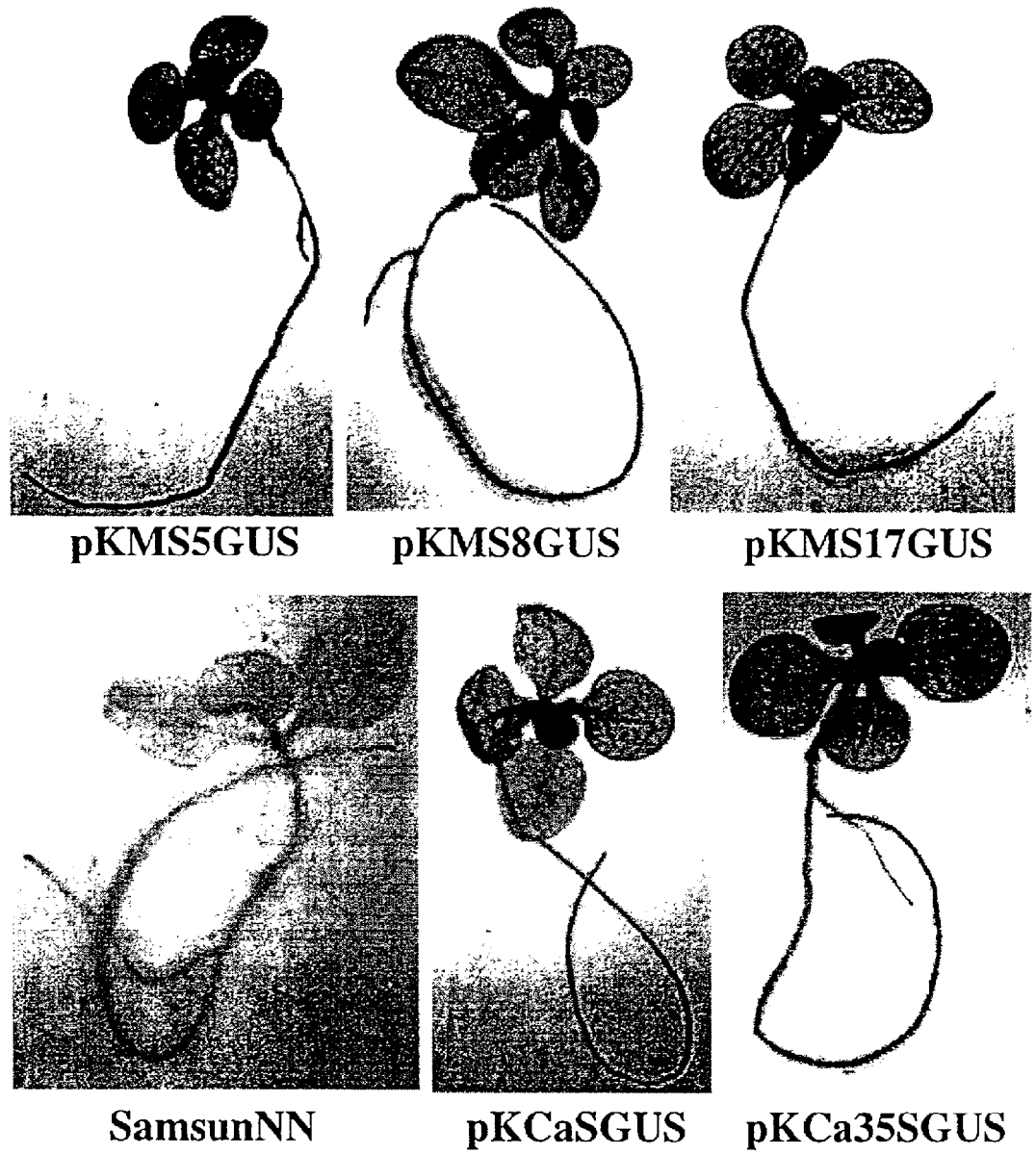

FIG. 7 provides photographs of six transgenic plants of the invention. Shown are histochemical assays of GUS expression in transgenic tobacco (N. tabacum cv. Samsun NN) seedlings (R1 progeny, 24-day old) developed for the following constructs: pKMS5GUS, pKMS8GUS, pKMS17GUS, pKCaSGUS (19S-GUS) and pKCa35SGUS (35S-GUS). These data were derived from pools of transformed lines with best expressing independent lines shown representing each construct. Untransformed control is shown wild type N. tabacum Samsun NN.

Figure 8:
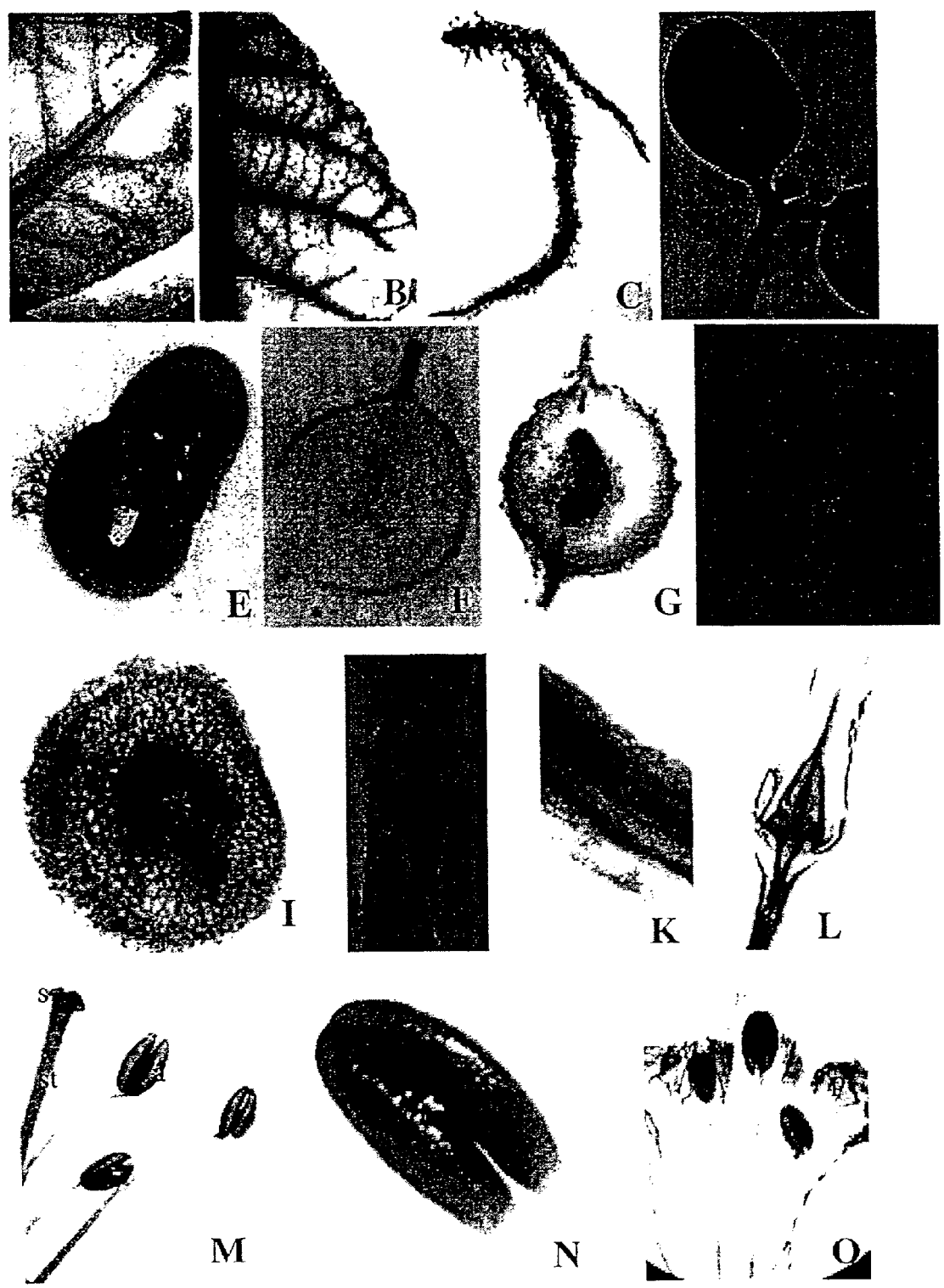

FIG. 8 provides photographs of parts of transgenic plants of the invention. Histochemical localization of GUS activity in developing transgenic tobacco plants expressing the GUS reporter gene directed by MMV Sgt promoter is shown. All sections are at 15× magnification. A. Samsun NN tobacco plant (non-transformed) as control; note no GUS staining. B. Matured leaf section from thirteen-weeks-old plants (R1 progeny) developed for the construct pKMS5GUS; note more GUS staining in vascular tissues (v), midrib and veins. C. Root from four-week-old seedlings (pKMS5GUS, R1 progeny) showing intense staining at the tip and in vascular (v) tissue. D. Top portion of ten-day old seedling (pKMS5GUS, R1 progeny); most GUS activity localized in leaves and apical meristematic (m) region. E. Transgenic tobacco seedling (pKMS5GUS, R1 progeny) at day 7 after imbibition, grown axenically on agar plate; GUS activity is localized primarily in root tips, root hairs and in the lower hypocotyls. F and G. Transverse cross section of petiole from control non-transformed Samsun NN (F), no GUS staining; and from four week-old seedlings (pKMS5GUS, R1 progeny), GUS staining is most intense in the vascular (v) cells (G). H, I, J and K. Transverse cross section (H and I) and longitudinal cross section (J and K) of stem from four week old control seedlings nontransformed Samsun NN (H and J respectively), note no GUS activity; and from four week old transformed seedlings (pKMD5GUS, R1 progeny); GUS activity localized mostly in vascular (v) tissues (I and K). L. Transverse section of tobacco flower pedicel and ovary; M. Stigma (s) and style (St); N. Anther (a); and O. The petal (p) and another (a) in flower tissues display GUS staining.

DETAILED DESCRIPTION OF THE INVENTION

The present invention is directed to (i) the isolation and characterization of the promoter for the subgenomic transcript (Sgt) from a genomic clone of *mirabilis mosaic* virus (Richins and Shepherd, 1983) as described below in Example 1, (ii) use of the MMV Sgt promoter to transform plant cells, plant expression vectors including a MMV Sgt promoter, chimeric genes including a MMV Sgt promoter sequence, and transgenic plants, plant cells, and plant parts, including seeds, which contain the MMV Sgt promoter in a chimeric gene.

Disclosed herein is the identification and characterization of a subgenomic transcript (Sgt) promoter from the *Mirabilis mosaic* virus (MMV), newly described species of the genus *Caulimovirus*. The optimal boundries required for maximal promoter activity and boundries that provided sub-maximal promoter activity have been defined by 5'-and 3'-end delation analysis of the promoter/leader region, both in transgenic plants and in protoplast transient expression experiments. The nucleotide sequence of the MMV Sgt promoter, containing a 12 nucleotide insert between nt −130 and −117 is shown in FIG. 1 (SEQ ID NO:11). It is understood that the MMV Sgt promoter described herein does not contain the 12 nt insert in nature and that the isolated Sgt promoter and promoter fragments described herein do not require the 12 nt insert for function. The insert was added for ease of manipulation of the isolated promoter and fragments. It is also understood, that all references to the nucleotide sequence of the isolated promoter and fragments thereof include the 12 nt insert as shown in FIG. 1, unless otherwise indicated. However, the invention also encompasses the MMV Sgt promoter and fragments thereof that lack the 12 nt insert and whose sequence numbering is adjusted accordingly, i.e., nt−130 is linked to nt−117. For example, SEQ ID NO:12 is the sequence of the MMV Sgt promoter from nt−646 to +377, but lacking the 12 nt insert.

A 333 nt MMV Sgt promoter fragment (sequence −306 to +27 from transcription start site (SEQ ID NO:2); 321 nt without the 12 nt insert shown in FIG. 1) (SEQ ID NO:13) was found to be sufficient for maximal promoter activity in a protoplast transient expression system. (FIG. 3). A larger promoter fragment containing nucleotides −456 to +27 (SEQ ID NO:9) showed even higher activity in stably transformed transgenic plants. (FIG. 5). Various other Sgt promoter fragments that retain promoter activity, albeit at a lower level than the full length or 333 bp fragment, have also been identified. (FIG. 3). Fragment 1 (−646 to +27) is SEQ ID NO:14. Fragment 2 (−606 to +27) is SEQ ID NO:15. Fragment 3 (−556 to +27) is SEQ ID NO:16. Fragment 4 (−506 to +27) is SEQ ID NO:17. Fragment 5 (−456 to +27) is SEQ ID NO:9. Fragment 6 (−406 to +27) is SEQ ID NO:18. Fragment 7 (−356 to +27) is SEQ ID NO:19. Fragment 8 (−306 to +27) is SEQ ID NO:2. Fragment 9 (−256 to +27) is SEQ ID NO:20. Fragment 10 (−206 to +27) is SEQ ID NO:21. Fragment 11 (−156 to +27) is SEQ ID NO:22. Fragment 12 (−117 to +27) is SEQ ID NO:23. Fragment 13 (−94 to +27) is SEQ ID NO:24. Fragment 14 (−74 to +27) is SEQ ID NO:25. Fragment 15 (−44 to +27) is SEQ ID NO:26. Fragment 16 (−456 to −74) is SEQ ID NO:27. Fragment 17 (−456 to −19) is SEQ ID NO:28. Fragment 18 (−306 to +50) is SEQ ID NO:29. Fragment 19 (−306 to +77) is SEQ ID NO:30. Fragment 20 (−306 to +127) is SEQ ID NO:31. Fragment 21 (−306 to +177) is SEQ ID NO:32. Fragment 22 (−306 to +227) is SEQ ID NO:33. Fragment 23 (−306 to +277) is SEQ ID NO:34. Fragment 24 (−306 to +327) is SEQ ID NO:35. Fragment 25 (−306 to +377) is SEQ ID NO:36.

The strength of the MMV Sgt promoter is compatible with the MMV FLt promoter and greater than that of the CaMV 19S and CaMV 35S promoters. This is the first report, to our knowledge, documenting the strong and constitutive expression characteristic of the MMV Sgt promoter.

The MMV Sgt promoter sequence contains several regulatory domains found in other caulimovirus promoters: the TATAA sequence (coordinates −65 to −61 from the Transcription Start Site (TSS) in FIG. 1) and the CAAT sequence (coordinates −110 to −70 from TSS in FIG. 1) located 41 bp upstream of the TATA box. In the MMV Sgt promoter sequence, an 'as-1'-like enhancer element (TGACG; coordinates −90 to −88 from TSS in FIG. 1) and an 'as-2'-like motif (GATT; coordinates −145 to −142 from TSS in FIG. 1) are located at the 22 bp and 76 bp upstream of the TATA box, respectively. The MMV Sgt promoter has only one copy of an 'as-1'-like or 'as-2'-like motif; whereas, duplicated copies are present in full-length transcript promoters of CaMV, FMV and MMV [13, 18, 22]. In addition, several direct repetitive sequences are present in the MMV Sgt promoter. These are: TCAGGA (−412 to −407 and −297 to −292), GAATTAC (−386 to −380 and −364 to −358), GGTGA (−244 to −240 and −344 to −340), CC(A/T)TTTTC (−77 to −69 and −19 to −11) and AAACA (−28 to −24, +12 to +16, and +21 to +25) (FIG. 1). These repetitive sequences may have some regulatory function.

An EcoRI site located at 48 bp upstream of the TATA sequence was modified to a SmaI site using a SmaI adaptor. This change inserted 12 additional nucleotides (5'-AATTACCCCGGGC-3') (SEQ ID NO:11), into the MMV Sgt promoter sequence as shown in lowercase (FIG. 1),— but did not affect promoter activity.

A comparison of the activity of a promoter fragment containing nucleotides −406 to +27 (SEQ ID NO:18) to that of a fragment containing nucleotides −356 to +27 (SEQ ID NO:19) shows that the inclusion of the nucleotide sequence from −406 to −356 enhances promoter activity. (FIG. 3A and B). Thus, it appears that the sequence −406 to −357 (SEQ ID NO:10) contains a promoter enhancer. This enhancer sequence can be used with other plant promoters to enhance promoter activity. For example, the enhancer sequence can be operably linked to a plant promoter either alone, or in combination with other promoter enhancer elements. Several enhancer elements may be operably linked, preferably in tandem, or may be spaced apart from one another, depending on the particular level of activity desired. The enhancer element may also be used with fragments of the present promoter to increase activity thereof.

In *Caulimovirus,* both subgenomic and full-length transcript promoters share the same 3'-ends by using the same poly (A) signal.

The transcriptional start site (TSS) of the MMV Sgt promoter was determined by primer extension analysis using total RNA isolated from transgenic plants developed with the construct pKMS5GUS (FIG. 2). The major extension product was detected and mapped to an adenine residue located 63 nucleotide downstream of the TATA box in the MMV Sgt sequence and, most likely, it represents the 5'-end of the MMV Sgt transcript (FIG. 2). The location of the TSS reported for other caulimoviruses: CaMV 35S [46], FMV34S [47], FMV FLt [18], PCISV FLt [7] and MMV FLt [22] is at the 32, 37, 45, 29 and 24 nucleotides downstream of respective TATA boxes. The transcription start site of the MMV Sgt promoter shows no sequence homology with that of other caulimovirus promoters.

A deletion analysis scheme of the MMV Sgt promoter is shown in FIG. 3A. A series of 5'-and 3'-end -deleted promoter fragments (total of 25 fragments) were included to map the optimal boundries required for maximal expression from the promoter/leader region and also to analyze the influence of the upstream and downstream cis-sequences with respect to the TATA box. The designed deletion promoter fragments 1 to 25 (FIG. 3A) were amplified by PCR and cloned into the expressing sites of vector pUCPMAGUS, as described in the Examples. Results of the expression analysis of the MMV Sgt promoter are shown in FIG. 3B. In a transient expression assay, construct 8 (pPMS8GUS), which contains the promoter fragment (coordinate−306 to +27 from TSS (SEQ ID NO:2)) gave maximum activity in protoplasts. The expression level of 5' deletion constructs 1, 2, 3 and 4 was 6%, 5%, 9% and 5%, respectively relative to construct 8. This suggest that the upstream sequence region (coordinates −646 to −455 from TSS in FIG. 1) may contain repressor elements. However, in this context, to obtain maximal promoter activity this region (coordinates −646 to −455 from TSS in FIG. 1) is not essential. The 5' deletion construct 5, 6 and 7 showed 88%, 60% and 32% of maximal activity, respectively. In construct 7, 5' deletion of 50 bp of sequence (−406 to −356 from TSS in FIG. 1) reduced promoter activity by 46% relative to construct 6 (compared construct 6 and 7) and by 63% relative to construct 5 (compare construct 5 and 7). These deletion results clearly show the importance of this region (−406 to −357 from TSS; SEQ ID NO:10) in overall promoter activity. There are also two direct repeat sequences GAATTC (coordinates −386 to −380, and −364 to −358 from TSS) in this region. Although, constructs 8 with promoter sequences (−306 to +27 from TSS (SEQ ID NO:2)) showed maximum activity in protoplast transient expression experiments, construct 5 with promoter coordinates (−456 to +27 from TSS (SEQ ID NO:9)) exhibited more activity in stable expression assay in transgenic plants. Constructs 9, 10 and 11 gave 42%, 37% and 29%, respectively, of maximal activity compared to construct 8, demonstrating the importance of cis sequences between −306 to −255 from TSS, as deletion of this stretch reduced maximal promoter activity by 58% (compare construct 9 with construct 8). Construct 12, containing a CAAT sequence (coordinates −110 to −107 from TSS in FIG. 1), showed 58% of construct 8 activity. However, further deletion of 22 bp (coordinates −117 to −93 from TSS in FIG. 1) in construct 13 (which contains an 'as-1'-motif) reduced promoter activity to 14% of that of construct 8, and to 24% of that of construct 12, suggesting the importance of the CAAT box in this region for promoter function. The 5' deletion construct 13, which contains the 'as-1'-motif, construct 14, which contains the TATA like element, and construct 15, which lacks a TATA region, showed 14%, 3% and 1%, respectively, of maximal activity (compare with construct 8). This demonstrates the requirement of further additional TATA upstream sequences for full promoter activity. The 3' deletion-construct 16 (promoter coordinates −456 to −74 from TSS in FIG. 1 (SEQ ID NO:27), which is devoid of a TATA box showed no appreciable promoter activity, suggesting the importance of the TATAA sequence in the MMV Sgt promoter function. Although, the MMV Sgt promoter does not contain a eukaryotic consensus regulatory sequence, TATATAA, this result indicates that the TATAAA sequence in MMV Sgt promoter functions as a TATA box. The 3' deletion construct 17 (−456 to −19 in respect to TSS in FIG. 1 (SEQ ID NO:28)), showed about 33% of maximal promoter activity. In this context, construct 17 may produce transcripts with different TSS. Construct 18, 19, 20, 21, 22, 23, 24 and 25, with successively extended 3' leader sequence, gave significantly less activity (2%, 1%, 0.7%, 9%, 0.25%, 0.3%, 0.4%, and 0.3%, respectively) of full promoter activity. These results suggest that, in this context, the longer leader sequence +50 to +378 has a significant inhibitory effect on promoter function.

A 333 bp MMV Sgt promoter/leader fragment, sequence −306 to +27 from TSS (See FIG. 1)(SEQ ID NO:2), was found to be sufficient for maximal GUS expression. In contrast, in the FLt promoter from FMV and MMV, an extended leader sequence is required for maximum promoter activity [18,22].

Figures 4A, 4B:
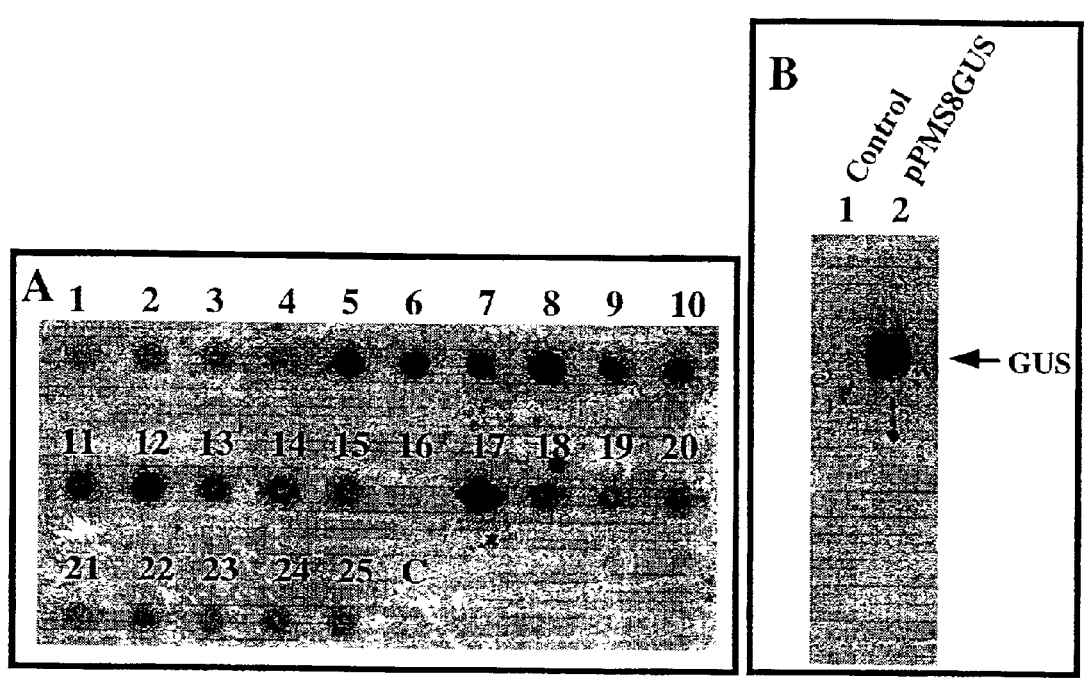

The relative strength of various MMV Sgt promoter fragments that were operably linked to the GUS reporter gene was evaluated by hybridization analysis of total RNA. Total RNA extracted from the transformed protoplasts with each of the constructs (No. 1 to 25, as described in FIG. 3A) was used for RNA dot-blot analysis (FIG. 4A). The P32-labeled GUS coding sequence was used as a probe. Construct 8 gave the strongest signal, and was followed by construct 5, 6, 7, 9, 10 and 17. A minimum signal was obtained from construct 16, which is devoid of a TATA-box (FIG. 4A). The relative transcript level obtained with these constructs, in general, is in good agreement with the observed GUS activity. The level of transcript in constructs 18 to 25 containing longer leader sequence (+50 to +378) was relatively less, and promoter function was reduced, probably through the effect of longer untranslated leader sequences on transcription and subsequent translation. Northern analysis of total RNA isolated from tobacco protoplasts transformed with construct 8 showed a single discrete band corresponding to GUS transcripts of the expected size (2100 nt) (FIG. 4B).

The present invention provides plant expression vectors and intermediate transforming vectors containing the subgenomic transcript (Sgt) promoter from MMV. The MMV Sgt promoter sequence is useful for directing and expressing foreign genes of interest, e.g., pathogen resistance genes, genes encoding metabolic proteins, gene encoding stress resistance factors, etc., in plants to confer useful properties to those transgenic plants, such as pathogen or stress resistance, for example. For example, the MMV Sgt promoter sequence may be operably linked to an insect resistance gene, such as the Bt toxin gene of *Bacillus thuringiensis*, a gene encoding phenol oxidase, a proteinase inhibitor, an alpha-amylase inhibitor, a chitinase, lectin, tobacco peroxidase, VIP1 or VIP2 of *Bacillus cereus*, tryptophan decarboxylase, cholesterol oxidase, or the wasp teratocyte secretory protein (TSP 14); an herbicide resistance gene, such as Mutated Acetolatate Syntase (ALS) from tobacco, bar gene (phosphinothricin acetyl tansferase from *Streptomyces hygroscopius*, 5-enolpyruvylshikimate-3 phosphate synthase, nitrilase gene (bxn) from *K. ozaenae*, or 2,4-dichlorophenoxyacetate monooxygenase from the soil bacterium *Alcaligenes eutrophus* (JMP 134); a fungal resistance gene, such as ribosome inhibiting proteins (RIP), ricin-A chain, wheat tritin, KP4 gene, or chitinase, or combinations thereof. In addition, there may be a transcriptional termination signal downstream of the coding sequence.

Where inhibition of gene expression is desired in a plant, the MMV Sgt promoter or fragments thereof can be operably linked to a polynucleotide coding sequence in antisense orientation so that the transcribed RNA is complementary in sequence to MRNA of the gene whose expression is to be inhibited. In addition, there may be a transcription termination sequence downstream of the polynucleotides directing synthesis of the antisense RNA.

These vectors are useful for both direct DNA uptake by isolated protoplasts and Ti plasmid-mediated gene transfer. Thus, the invention is applicable to plant genetic engineering in general.

For example, the MMV Sgt promoter constructs of the invention may comprise an intermediate plant transformation plasmid which has a region of homology to an *Agrobacterium tumefaciens* gene vector, an *Agrobacterium tumefaciens* T-DNA border region and a chimeric gene located between the T-DNA border and the region of homology. The chimeric gene prferably contains a MMV Sgt promoter of SEQ ID NO:1 or SEQ ID NO:12, or a fragment of SEQ ID NO:1 or SEQ ID NO:12 operably linked to a nucleotide sequence encoding a polypeptide in sense or antisense orientation. Fragments of the MMV Sgt promoter used in these constructs preferably have at least about 30% promoter activity (relative to the full length promoter), more preferably about 32% promoter activity, and most preferably, from about 60% to 100% promoter activity. The nucleotide sequence that is linked to the MMV Sgt promoter preferably encodes a heterologoud gene (heterologous relative to the promoter). Preferably, the construct does not include any sequence encoding MMV polypeptide.

The present invention also provides plant transformation vectors, comprising a disarmed *Agrobacterium tumefaciens* plant tumor-inducing plasmid and a chimeric gene. The chimeric gene contains a MMV Sgt promoter of SEQ ID NO:1 or a fragment thereof having at least about 30% promoter activity relative to a full length promoter, preferably about 32% activity, and most preferably, about 60% to about 100% promoter activity. The promoter is operably linked to a nucleotide sequence which encodes a polypeptide, preferably a heterologous peptide or polypeptides (relative to the MMV promoter). In another preferred embodiment, the chimeric gene contains a MMV Sgt promoter of SEQ ID NO:12, or a fragment thereof operably linked to a nucleotide sequence encoding a polypeptide, wherein the fragment has at least about 30% promoter activity relative to the full length promoter of SEQ ID NO:12).

The MMV Sgt promoter-containing DNA molecules, plasmids and vectors of the invention can be used to generate stable transgenic plants or transform plant protoplasts. Methods for transforming plant protoplasts and generating transgenic plants are well known in the art of plant molecular engineering. For generating transgenic plants or plant protoplasts, the MMV Sgt promoter of the invention, which has a nucleotide sequence of SEQ ID NO:1 or SEQ ID NO:12, or a fragment of SEQ ID NO:1 or SEQ ID NO:12 that has at least about 30% promoter activity, preferably about 32% promoter activity, more preferably about 60% promoter activity, and most preferably up to 100% promoter activity, is operably linked to an open reading frame encoding a polypeptide of interest. In a preferred embodiment, the MMV Sgt promoter-open reading frame construct also includes a 5'-leader sequence and/or a non-translated polyadenylation site operably linked thereto. Preferably, promoter-containing constructs of the invention include at least one enhancer domain in the promoter region, and most preferably, the promoter-containing constructs of the invention include two or more enhancer domains.

The MMV Sgt constructs of the invention can be used to generate transgenic plants in any type of plant, i.e., monocots or dicots. Preferably, transgenic plants of the invention are crop plants, such as tobacco, hemp, or food crops, such as tomato, corn, soy, wheat, rice, etc. Transgenic plants of the invention may also be flowering plants, such as carnations, roses, and the like. The skilled practitioner, using methods known in the art, can readily transform any plant type using the isolated DNA molecules and vectors of the invention. For example, a transgenic plant of the invention can be produced using *Agrobacterium tumefaciens* mediated DNA transfer, preferably with a disarmed T-DNA vector, electroporation, direct DNA transfer, and particle bombardment. Techniques are well known in the art for introducing nucleic acids into monocots as well as dicots, as are the techniques for culturing such plants and plant tissues and regenerating them.

The MMV Sgt promoter constructs of the present invention can be used to generate transgenic plants, seeds or protoplasts, and may be used to drive expression of a gene or genes of interest in any plant tissue, e.g., roots, stems, leaves, flowers, stems, pollen, or seeds.

The studies presented herein demonstrate that the MMV Sgt promoter is a strong constitutive promoter capable of directing foreign gene expression in heterologous systems, including transgenic plants, at a greater level than that of both CaMV35S and CAMV 19S promoters. There is very limited sequence homology between the MMV Sgt promoter with other caulimovirus promoters, although they are functionally analogous.

The present MMV Sgt promoter and fragments of the promoter are useful for generating transgenic plants and, for example, studying plant metabolism. For metabolic engineering, expression of multiple genes in a single cell may be necessary to gain an understanding of plant metabolic pathways. The use of different promoters having non-homologous sequences may be useful in order to avoid genetic instability due to recombination between identical promoter sequences. Thus, the present MMV Sgt promoter constructs will lend themselves handily to such studies, when used to drive the expression of a plant metabolic gene or genes in conjunction with other chimeric constructs driven by other, nonhomologous promoters.

The present invention is illustrated by the following examples, but is not intended to be limited thereby.

EXAMPLE 1

Protoplasts, Plants and Enzymes

Isolation of protoplasts from tobacco cell suspension cultures (Xanthi 'Brad') and electroporation of protoplasts with supercoiled DNA containing a promoter fragment fused with the GUS gene were done essentially as described by [38]. Tobacco plants (*Nicotiana tabacum* cv. Samsun NN) were used for plant transformations. Restriction enzymes, antibiotics, components of plant tissue culture medium, and RNA isolation kits were purchased from commercial sources. Nitrocellulose and Nytran membranes were obtained from Schleicher & Schuell, USA.

Isolation of a MMV Sgt Promoter and Modification of its DNA Sequence

A full-length genomic clone of *mirabilis mosaic* virus (MMV) in plasmid pMMV-B10 [1] has been fully sequenced (Maiti, unpublished results), and was used as template for PCR reactions. A 1012 bp segment (coordinates 4829 to 5840 of the MMV genome) was selected for promoter deletion analysis. The fragment was isolated as a BamHI-HindIII fragment by PCR using the following primers: (i) Forward primer: 5'-GCG GGC GGA TCC GAAAAA CGG AAA CCG TTA-3' (SEQ ID NO:3) and (ii) Reverse primer: 5'-ATG CAG AAG CTT TTG TTG TGT CTT TAC CGG-3' (SEQ ID NO:4). Promoter sequences in the primers are shown in bold and restriction enzymes sites are underlined. The PCR-fragment was gel-purified using QIAGEN procedure (Valencia, Calif. 91355, USA). After digestion with BamHI and HindIII, the PCR fragment was cloned into the corresponding sites of pBS(KS+) (Strategen, La Jolla, Calif. 92037, USA). The plasmid was designated as pBSMS1011.

Modification of EcoRl site to a Smal site

The pBSMS1011 has an EcoRI site at the MMV genome coordinate 5345. This EcoRI site located 52 bp upstream of a TATA sequence was modified with a SmaI site using two primers having the following sequences: Forward primer has sequence 5'-AATTACCCGGGC-3' (SEQ ID NO:5) and reverse primer has sequence 5'-AATTGCCCGGGT-3' (SEQ ID NO:6). These two primers were mixed in a 1:1 molar ratio and allowed to anneal by slow cooling (2° C./min) from 94° to 24° under a programmed PCR cycle. The plasmid pBSMS1011 was digested with EcoRI and ligated with the 'EcoRI to SmaI' adapter, followed by transformation. The resulting plasmid was designated as pBSMS1011E. This change inserted 12 additional nucleotides (5'-AATTACCCGGGC-3') (SEQ ID NO:5) into the promoter sequence (FIG. 1).

DNA Sequencing

Automated DNA sequencing was done with an Applied Biosystem ABI Prism 310 Genetic Analyzed (Perkin Elmer) using ABI Prism Dye terminator cycle sequencing ready reaction kit containing Ampli Taq DNA polymerase. Primer extension was carried out by using PCR (denaturation 96° C. for 30 seconds; annealing 50° C. for 30 seconds and extension at 60° C. for four minutes; 27 cycles five nmole template DNA and 50 pmole specific primer in 20 $\mu$l of reaction mix. After PCR excess terminators were removed by 95% ethanol wash. The pellet containing the purified extension products was finally suspended in 25 $\mu$l of template suspension reagent (P/N401674; Perkin Elmer), vortexed, and heat-denatured at 95° C. for two minutes before loading into a capillary tube.

Glucuronidase (GUS) Assay

Fluorometric GUS assays to measure GUS activity in plant tissue or protoplasts extracts and histochemical GUS staining to localize the distribution of GUS activity in plants were performed according to Jefferson et al., [42], as described earlier [18]. Protein in plant extract was determined according to the method of Bradford [43], using BSA as a standard.

RNA Extraction, RNA Dot Blot and Northern Blot Analysis

Total RNA was prepared from transformed protoplasts containing individual MMV Sgt promoter constructs by extracting with guanidine thiocyanate [44] solution using an Ambion RNA extraction kit (RNAqueous), as described earlier [22]. The RNA dot blot and Northern blot analysis were performed using a 32P-labeled GUS-probe essentially, as described previously [22].

Determination of Transcriptional Start Site (TSS) of MMV Sgt Promoter

The transcriptional start site was determined by primer extension analysis. The extension product was separated on a 7.5% polyacrylamide gel containing 7M-urea [45]. Sequencing reactions were carried out according to Sanger et al. [39], using Sequenase Version 2.0, USB, as described earlier [22].

EXAMPLE 2

Construction of Vectors for Transient Expression Experiment in Protoplasts

A series of promoter fragments used in construction of the plant transformation vector with the subgenomic promoter of MMV were designed to study the influence of upstream and downstream sequences with respect to the TATA box on promoter activity. The defined MMV Sgt promoter sequence, of length as indicated (in FIG. 1) was amplified by PCR using pBSMS1011E as template and appropriately designed primers to tailor an EcoRI site at the 5'-end and HindIII site at the 3'-end of the amplified products. PCR amplification was carried out for 31 cycles under the following standard conditions: denaturation (92° C. for 1 minute), annealing (55° C. for 1 minute), extension (72° C. for 2 minutes) using ELONGASE enzyme mix (recombinant high fidelity TaqDNA polymerase mix with proof reading 3'-5' exonuclease activity from Gibco-BRL, Maryland, USA. Each of PCR amplified fragments 1 to 25 was restricted with EcoRI and HindIII; the restricted fragments were gel-purified and cloned into the corresponding sites of pUC119 vector and sequenced by dideoxy chain terminator method [39] using synthetic primers.

Subcloning of the MMVSgt Promoter Fragments from pUC119 into pUCPMAGUS Vector

The sequence of each of the MMV Sgt promoter fragments cloned in pUC119 was verified before subcloning to pUCPMAGUS, a protoplast expression vector (Dey and Maiti, 1999). MMV Sgt promoter fragments were individually gel purified from the corresponding pUC119 clone after restriction digestion with EcoRI and HindIII and subcloned into the corresponding sites of pUCPMAGUS (Dey and Maiti, 1999). The following deletion plasmids were developed (see FIG. 2). The 5' and 3' coordinates of the promoter fragment with respect to TSS are given in parenthesis: pPMS1GUS (−646 to +27 (SEQ ID NO:14)), pPMS2GUS (−606 to +27(SEQ ID NO:15)), pPMS3GUS (−556 to +27 (SEQ ID NO:16)), pPMS4GUS (−506 to +27(SEQ ID NO:17)), pPMS5GUS (−456 to −27(SEQ ID NO:9)), pPMS6GUS (−406 to +27(SEQ IN NO:18)), pPMS7GUS (−356 to +27(SEQ ID NO:19)), pPMS8GUS (−306 to +27 (SEQ ID NO:2)), pPMS9GUS (−256 to +27(SEQ ID NO:20)), pPMS10GUS (−206 to +27(SEQ ID NO:21)), pPMS11GUS (−156 to +27(SEQ ID NO:22)), pPMS12GUS (−117 to +27(SEQ ID NO:23)), pPMS13GUS (−94 to +27 (SEQ ID NO:24)), pPMS14GUS (−74 to +27(SEQ ID NO:25)), pPMS15GUS (−44 to +27(SEQ ID NO:26)), pPMS16GUS (−456 to −74(SEQ ID NO:27)), pPMS17GUS (−456 to −19(SEQ ID NO28)), pPMS18GUS (−306 to +50(SEQ ID NO:29)), pPMS19GUS (−306 to +77(SEQ ID NO:30)), pPMS20GUS (−306 to +127(SEQ ID NO:31)), pPMS21GUS (−306 to +177(SEQ ID NO:32)), pPMS22GUS (−306 to 227(SEQ ID NO:33)), pPMS23GUS (−306 to 227(SEQ ID NO:34)), pPMS24GUS (−306 to +327(SEQ ID NO:35)), pPMS25GUS (−306 to +377(SEQ ID NO:36)), Construction of Vectors with MMV Sgt Promoter Fragments for Expression of Genes in Plants The MMV Sgt promoter fragments from constructs pPMS5GUS (−456 to +27), pPMS8GUS (−306 to +27) and pPMS17GUS (−456 to −19) were isolated by EcoRI and HindIII digestion followed by gel purification and cloned into the plant expression vector pKYLX71 [40] individually at its unique restriction EcoRI and HindIII sites that flank the promoter. The following plant gene expression vectors were developed: pKMS5, pKMS8 and pKMS17. These plant gene expression vectors have multiple cloning sites (MCS): 5'-HindIII-BamHI-XhoI-SstI-XbaI-3') with the following unique sites: HindIII, XhoI, SstI and XbaI. The reporter GUS gene from pBSGUS was inserted as an XhoI-SstI fragment into these pKYLX-based expression vectors separately, and the resulting plasmids were designated as pKMS5GUS, pKMS8GUS and pKMS17GUS.

Isolation of CaMV 19S Promoter, and Construction of Vectors with the CaMV 19S and 35S Promoters for Transient and Stable Expression of Genes in Plant Cells A 990 bp SalI to SstI fragment containing the CaMV 19S promoter was isolated from pCaMV10, a full length genomic clone of the CaMV strain CM1841 [3]. This SalI to SstI restricted fragment, corresponding to the CaMV genomic coordinates 4833 to 5822, was gel-purified and cloned into the corresponding sites of pBS(KS+). The resulting plasmid was designated as pBSCaMV (4833–5822). An internal EcoRI site in the pBSCaMV (4833–5822) corresponding to the CaMV genomic coordinate 5646 was modified to SmaI site using the synthetic adaptor, and the modified plasmid was designed pBSCaMV (4833–5822)E. Using this clone as a template, a 412 bp CaMV 19S promoter fragment (CaMV coordinates 5380 to 5773) was isolated by PCR with the designed primers. The forward primer, 5'CAAGAATTCGTTAAC AAGCTGCAGAAAGGAATTACC-3' (SEQ ID NO:7), contains EcoRI and HpaI sites (underlined) and CaMV sequence (shown in bold). The reverse primer 5'-CTTAAGCTTGCTTGGAGGTCTGATTTT-3' (SEQ ID NO:8), has a HindIII site (underlined) and CaMV sequence (indicated in bold). The PCR-amplified promoter fragment has EcoRI and HpaI sites at the 5'-end and a HindIII site at the 3'-end to facilitate cloning. The fragment has the general structure 5'-EcoRI-HpaI-promoter sequence SmaI-TATA-promoter sequence-HindIII-3'.

The PCR amplified CaMV 19S promoter fragment (412 bp) was cloned into the corresponding EcoRI-HindIII sites of the vector pUCPMAGUS [22] for the transient expression in protoplasts, and also into the corresponding sites of the vector pKYLXGUS for stable transgene expression. The resulting expression vectors were named pPCaSGUS and pKCaSGUS, respectively.

Similarly, the CaMV 35S promoter (−940 to +27 from TSS; corresponding to the CaMV genomic coordinates 6493 to 7459), was cloned as an EcoRI-HindIII fragment into the corresponding sites of the transient expression vector (pUCPMAGUS) for the expression of GUS gene in protoplasts. The resulting plasmid was named pPCa35S-GUS. The GUS reporter gene was inserted as an XhoI-SstI fragment into the corresponding sites of PKYLX71 [40]. In the resulting plant expression vector pKCa35S-GUS, the GUS reporter gene is directed by the CaMV 35S promoter (coordinates −940 to +27 from TSS).

EXAMPLE 3

Transient Expression Analysis of MMV Sgt Promoter Deletion Constructs in a Protoplast System Isolation of protoplasts from the tobacco cell suspension cultures (Xanthi 'Brad') and electroporation of protoplasts with supercoiled DNA containing the MMV Sgt promoter fragment and GUS gene were done essentially as described earlier (Maiti et al., 1998). Electroporation was carried out by using the GenePulser II Apparatus (BioRad) with the Capacitance Extender II (Model 165-2107). An aliquot of 800 1 containing $2 \times 10^6$ protoplasts in an electroporation cuvette (0.4 cm electrode gap) was electroporated (200V used for charging 960 F capacitance for 40 milliseconds) with 5 g of supercoiled plasmid DNA containing GUS reporter gene. After 20 hours, two billion electroporated protoplasts were individually harvested for GUS assay. A deletion analysis scheme of MMV Sgt promoter is shown in FIG. 3A. A series of 5'-and 3'-end deleted promoter fragments (total 25 fragments) were included in order to map the optimum boundaries required for maximal expression from promoter/leader region and also to analyze the influence of the upstream and downstream cis-sequence with respect to the TATA box. The designed deletion promoter fragments 1 to 25 (as shown in FIG. 3A) were amplified by PCR and cloned into protoplasts expressing vector pUCPMAGUS as in Example 2. Results of the expression analysis of the MMV Sgt promoter are shown in FIG. 3B. In a transient expression assay, the construct pPMS8GUS, which contains the promoter fragment (coordinates −306 to +27 from TSS) gives maximum activity. The construct pPMS5GUS, pPMS7GUS, pPMS10GUS and pPMS17GUS showed 76%, 70%, 65% and 45% of GUS activity compared to the constructs pPMS8GUS (with highest GUS activity). Construct pPMS16GUS, which is devoid of the TATA box, showed very little of GUS activity indicating the importance of TATA element in MMV Sgt promoter activity. A 320 bp MMV Sgt promoter/leader fragment, sequence −306 to +27 from TSS, was found to be sufficient for maximal GUS expression. Constructs pPMS5GUS, pPMS8GUS and pPMS17GUS were selected for their stable expression analysis in transgenic tobacco plants (see Example 4).

EXAMPLE 4

Stable Expression Analysis of MMV Sgt Promoter in Transgenic Plants

The MMv Sgt promoter fragments from constructs pPMS5GUS (−456 to +27), pPMS8GUS (−306 to +27) and pPMS17GUS (−456 to −19) were isolated by EcoRI and HindIII digestion followed by gel purification and cloned into the plant expression vector pKYLX71 (Schardl et al., 1987) separately at its unique EcoRI and HindIII restriction sites that flank the promoter. The following plant expression vectors were developed: pKMS5, pKMS8 and pKMSl7. These plant expression vectors have multiple cloning sites (MCS): 5'-HindIII-BamHI-XhoI-SstI-XbaI-3') with the following unique sites: HindIII, XhoI, SstI and XbaI. The reporter GUS gene from pBSGUS as XhoI-SstI fragment was inserted into these pKYLX-based plant expression vectors separately and the resulting plasmids were designated as pKMS5GUS, pKMS8GUS and pKMS17GUS.

On average, twelve to fourteen independent primary transgenic tobacco (Nicotiana tabacum cv. Samsun NN) lines ($R_o$ progeny) were developed for each of these constructs and grown under greenhouse condition. Leaf extract from these $R_O$ plants was used for fluorometric GUS assays. Analysis of these lines from $R_O$ progeny showed that the GUS expression level in transgenic plant lines obtained from pKMSSGUS construct is maximum followed by plant lines obtained from construct pKMS8GUS (82% of pKMS5GUS activity) and pKMS17GUS (48% of pKMS5GUS activity), (data not presented for Ro plants)). Seeds were collected from self-fertilized independent Ro lines. Segregation analysis for the marker gene ($Kan^R$) were performed. About 8 to 9 individual $R_1$ transgenic lines showing expected segregation ratio ($Kan^R$:$Kan^S$=3:1) for the marker $Kan^R$ for each construct were further analyzed. Whole seedling extract was used for fluorometric GUS assays. The GUS activity in $R_1$ transgenic plants (FIG. 3B). is however 5 to 8 times higher than the GUS activity obtained in $R_O$ plants. Transgenic plants (R1 progeny) developed for construct pKMS5GUS showed highest activity followed by pKMS8GUS (−306 to +27, 58% of pKMS5GUS) and pKMS17GUS (−456 to −19, 32% of pKMS5GUS). Histocherical GUS staining was carried out with whole seedlings separately from these three constructs showed comparable intensity of GUS activity (FIG. 4).

EXAMPLE 5

Comparative Expression Analysis of MMV Sgt Promoter with MMV FLt, CaMV 35S and CaMV19S Promoters.

In pPCaSGUS or pKCaSGUS, the GUS reporter gene is directed by the CaMV sub-genornic transcript promoter sequence (corresponding to CaMV genomic coordinates 5380 to 5773). The MMV Sgt promoter constructs pKMS5GUS, pKMS8GUS and pKMS17GUS were compared with the CaMV promoters (19S and 35S) and three MMV FLt promoter constructs pKM1GUS, pKM12GUS and pKM13GUS (Dey and Maiti 1999a) both in protoplasts assay (FIG. 5A), and transgenic plant expression analysis (FIG. 5B). In protoplast assays, the MMV Sgt promoter fragments in constructs, pPMS5GUS and pPMS8GUS, showed more activity (5 and 7 fold, respectively) as compared to pPCaSGUS, and about two fold greater activity than CaMV 35S promoter (FIG. 5A). MMV Sgt promoter in pPMS5GUS and pPMS8GUS showed comparable activity with MMV FLt promoter in pPM12GUS and pPM13GUS (FIG. 5A), suggesting that the strength of the MMV Sgt promoter is comparable to or greater that of the MMV FLt promoter. The CaMV 19S is a weakpromoter, as compared to the 35S promoter [14]. This suggests that the MMV Sgt promoter may have a different functional mechanism, as compared to the CaMV 19S promoter.

For stable transformation assays, a number of independent transgenic tobacco (Nicotiana tabacum cv. Samsun NN) lines were generated. Flurometric GUS assays were carried out with whole seedling (R1 progeny) extracts. The results of transgenic plant analysis shown in FIG. 5B. In protoplast assays the GUS expression with construct pPMS8GUS was highest. Three MMV Sgt promoter fragments analyzed in transgenic plants showed strong GUS expression compared to both CaMV 19S and 35S promoter. The level of expression of GUS reporter gene in pKMS5GUS (highest expressing construct) is about 8 fold more than CaMV 19S promoter and 2 fold stronger than CaMV 35S promoter (FIG. 5B).

The relative intensity of histochemical GUS staining of the young seedlings developed for the constructs, pKMS5GUS and pKMS8GUS, pKMS17GUS showed strong promoter activity compared to pKCaSGUS (with CaMV35S promoter) and pKCa35SGUS (with CaMV 35S promoter) (FIG. 4).

EXAMPLE 6

Constitutive Expression of MMVSgt Promoter in Different Parts of Transgenic Seedlings The MMV Sgt promoter activity was measured in various tissues during seedling (R1 progeny, second generation) development. Transgenic seedlings were aseptically grown on MS-agar medium in presence of kanamycin (240μg/ml) supplemented with 3% sucrose. Seedlings from the independent lines showing segregation ratio ($Kan^s$:$Kan^r$=1:3) for the Kan[r] gene were selected for further analysis. Eight independent lines for each construct were examined. The relative expression of GUS reporter gene in 28 day (4 weeks) old seedlings ($R_1$ progeny) transformed with pKMS5GUS, pKMS8GUS and pKMS 17GUS were monitored by fluorometric GUS assay and by histochemical staining. A relative level of GUS activity in roots, leaves and stems is shown in FIG. 5. On average GUS activity was maximum in roots followed by in leaves and stems in seedling developed for pKMS5GUS. Seedlings developed with pKM8GUS showed more activity in leaves followed by in roots and stems. Seedlings developed for construct pKMS15GUS showed more uniform GUS activity in different parts of seedlings although slightly more activity in leaves followed by stems and roots (FIG. 5).

EXAMPLE 7

Histochemical Localization of GUS Activity in Transgenic Plants

MMV Sgt promoter activity was measured in various tissues during seedling (R1 progeny, second generation) development. The level of intensity of GUS activity was measured by histochemical staining of hand-cut fresh tissue sections of various organs of transgenic plants developed for the construct pKMS5GUS shown in FIG. 8. Strong GUS activity was detected in vascular tissues in midrib and lateral secondary veins of matured leaves (FIG. 8B), in young leaves and in the apical meristem region of young seedlings (FIG. 8D). Cross section of stems (FIG. 8I) and petioles (FIG. 8G) showed intense staining of the phloem cells. Strong GUS accumulation was detected in vascular tissues of roots and root tips (FIG. 8C). The non-transformed tobacco showed no GUS staining in mature leaves (FIG. 8A), in root tissues (data not shown) or in cross sections of stems FIG. 8H), and petioles (FIG. 8F). Histochemical GUS staining of different floral tissues was performed. The petal (corolla) portion of the flower showed light GUS staining (FIG. 8O). Another, plant section containing pollen grains exhibited intense GUS activity (FIG. 8N). The stigma and style portion of the flower showed much less GUS staining (FIG. 8M). The longitudinal cross-section of the flower pedicel and ovary (6 days after opening of the flower) showed intense staining of the pedicel and the basal vascular part of the ovary (FIG. 8L). Differential GUS staining in various floral organs may be due to tissue specific expression of MMV Sgt promoter. A similar tissue specific expression pattern was documented for the FLt promoter from CaMV [30], FMV [18], PCISV [21] and MMV [22,23].

References

[1] Richins R D, Shepherd R J: Physical maps of the genome of dahlia mosaic virus and *mirabilis mosaic* virus—two members of the caulimovirus group. Virology 1983; 124: 208–214.

[2] Brunt A A, Kitajima E W: Intracellular location and some properties of mirabilis mosaic virus, a new member of the cauliflower mosaic group of viruses. Phytopath Z 1973; 76: 265–275.

[3] Gardner R C, Howarth A J, Hahn P, Brown-Leudi M, Shepherd R J, Messing J: The complete nucleotide sequence of an infectious clone of cauliflower mosaic virus by M13mp7 shotgun sequencing. Nucl Acids Res 1981; 9: 2871–2888.

[4] Hull R, Sadler J, Longstaff M: The sequence of carnation etched ring viral DNA:comparision with cauliflower mosaic virus and retroviruses. EMBO J 1986; 5: 3083–3090.

[5] Richins R D, Scholthof H B, Shepherd R J: Sequence of figwort mosaic virus DNA (caulimovirus group). Nucl Acids Res 1987; 15: 8451–8466.

[6] Hasegawa A, Verver J, Shimada A, Saito M, Goldbach R, van Kammen A, Miki K., Kameya-Iwaki M, Hibi T: The complete sequence of soybean chlorotic mottle virus DNA and the identification of a novel promoter. Nucl Acids Res 1989; 17: 9993–10013.

[7] Richins R D: Organization and expression of the peanut chlorotic streak virus genome. Ph.D. Dissertation, 1993, University of Kentucky, Lexington Ky. (for the PCISV genomic sequence: DNA EMBL Data Library GenBank Accession Number U13988).

[8] Calvert L, Ospina M, Shepherd, R J: Characterization of cassava vein mosaic virus: a distinct plant pararetrovirus. J Gen Virol 1995; 76: 1271–1276.

[9] Petrzik K: Strawberry vein banding virus complete genome sequence, 1996, (Document ID 1360608), GenBank Accession Number X97304).

[10] Richert-Poggeler K R, Shepherd R J: Petunia vein-clearing virus: a plant pararetrovirus with the core sequence for an integrase function. Virology 1997; 236: 137–146.

[11] Odell J T, Dudley R K, Howell S H: Structure of the 19S RNA transcripts encoded by the cauliflower mosaic virus genome. Virology 1981; 111: 377–385.

[12] Driesen M, Benito-Moreno R M, Hohn T, Futterer J: Transcription from the CaMV19S promoter and autocatalysis of translation from CaMV RNA. Virology 1993; 195: 203–210.

[13] Odell J T, Nagy F, Chua N H: Identification of DNA sequences required for the activity of the of the cauliflower mosaic virus 35S promoter. Nature 1985; 313: 810–812.

[14] Lawton M A, Tierney, M A, Nakamura I, Anderson E, Komeda Y, Dube P, Hoffman N, Fraley R T, Beachy, R N: Expression of a soybean -conglycinin gene under the control of the cauliflower mosaic virus 35S and 19S promoters in transformed petunia tissues. Plant Mol Biol 1987; 9: 315–324.

[15] Bhattacharyya-Pakrasi M, Pen J, Elmer J S, Laco G, Shen P, Kaniewska M B, Kononowicz H, Wen F, Hodges T K, Beachy R N: Specificity of a promoter from the rice tungro baciliform virus for expression in pholem tissues. Plant J 1993; 4: 71–79.

[16] Medberry S L, Lockhart B E L, Olszewski N E: The Commelina yellow mottle virus promoter is a strong promoter in vascular and reproductive tissues. Plant Cell 1992; 4: 185–192.

[17] Gowda S, Wu F C, Herman H B, Shepherd R J: Gene VI of figwort mosaic virus (caulimorirus group) functions in post transcriptional expression of genes on the full-length RNA transcript. Proc Nafl Acad Sci USA 1989; 86: 9203–9207.

[18] Maiti I B, Gowda S, Kiernan J, Ghosh S K, Shepherd R J: Promoter/leader deletion analysis and plant expression vectors with the figwort mosaic virus (FMV) full-length transcript (FLt) promoter containing single and double enhancer domains. Transgenic Research 1997; 6: 143–156.

[19] Sanger M, Daubert S, Goodman R M: Characteristics of a strong promoter from figwort mosaic virus: comparison with the analogous 35S promoter from cauliflower mosaic virus and the regulated mannopine synthase promoter. Plant Mol Biol 1990; 14: 433–443.

[20] Verdaguer B, de Kochko A, Beachy R N and Fauquet C: Isolation and expression in transgenic tobacco, and rice plants of the cassava vein mosaic virus (CVMV) promoter. Plant Mol Biol 1996; 31: 1129–1139.

[21] Maiti I B, Shepherd R J: Isolation and expression analysis of peanut chlorotic streak caulimovirus (PClSV)

[22] Dey N, Maiti I B: Structure and promoter/leader deletion analysis of mirabilis mosaic full-length transcript (FLt) promoter in transgenic plants. Plant Mol Biol 1999; 40: 771–782.

[23] Dey N, Maiti I B: Further characterization and expression analysis of mirabilis mosaic caulimovirus (MMV) full-length transcript promoter with single and double enhancer domains in transgenic plants. Transgenics 1999; 3: 61–70.

[24] Ow D W, Jacobs J D, Howell S H: Functional regions of the cauliflower mosaic virus 35S RNA determined by use of the firefly luciferase gene as a reporter of promoter activity. Proc Natl Acad Sci USA 1987; 84: 4870–4874.

[25] Benfey P N, Chua N H: The CaMV 35S enhancer contains at least two domains which can confer different developmental and tissue specific expression patterns. EMBO J 1989; 8: 2195–2202.

[26] Benfey P N, Chua N H: The cauliflower mosaic virus 35S promoter: combinatorial regulation of transcription in plants. Science 1990; 250: 959–966.

[27] Fang, R X, Nagy F, Sivasubramaniamn S, Chua N H: Multiple cis regulatory elements for maximal expression of the cauliflower mosaic 35S promoter in transgenic plants. Plant Cell 1989; 1: 141–150.

[28] Benfey P N, Ren L, Chua N H: Combinatorial and synergistic properties of CaMV 35S enhancer subdomains. EMBO J 1990; 9: 1685–1696.

[29] Benfey P N, Ren L, Chua, N H: Tissue-specific expression from 35S enhancer subdomains in early stages of plant development. EMBO J. 1990; 9: 1677–1684.

[30] Lam E: Analysis of tissue-specific elements in the CaMV 35S promoter, In Nover L (Ed.): Results and problem in cells differential, plant promoters and transcription factors. Springer-Verlag, Berlin/Heidelberg, 1994, Vol. 20, pp. 181–196.

[31] Holtrof S, Apel K, Bohlmann H: Comparision of different constitutive and inducible promoters for the overexpression of trarsgene in *Arabidopsis thaliana*. Plant Mol Biol 1995: 29: 637–646.

[32] Wilmink A, van de Ven B C E, Dons J J M: Activity of constitutive promoter in various species from the Liliaceae. Plant Mol Biol 1995; 28: 949–955.

[33] Mitsuhara I, Ugaki M, Hirochika H, Ohshima M, Murakami T, Gotoh Y, Katayose Y, Nakamura S, Honkura, R., Nishimiya, S., Uneo, K., Mochizuki, A., Tanimoto, H., Tsugawa, H., Otsuki, Y, Ohashi Y: Efficient promoter cassettes for enhanced expression of foreign genes in dicotyledonous and monocotyledonous plants. Plant Cell Physiol 1996; 37: 49–59.

[34] Assaad F F, Singer E R: Cauliflower mosaic virus 35S promoter activity in *Escherichia coli*. Mol Gen Genet 1990; 223: 517–520.

[35] Pobjecky N, Rosenberg G H, Dinter-Gottlieb G, Kaufer N F: Expression of the—glucuronidase gene under the control of the CaMV 35S promoter in *Schizosaccharomyces pombe*. Mol Gen Gent 1990; 220: 314–316.

[36] Zahm P, Seong-Iyul, R, Klaus G: Promoter activity and expression of sequence from Ti-plasmid stably maintained in mammalian cells. Mol Cell Biochem 1989; 90: 9–18.

[37] Ballas N. Shimshon B, Hermona S, Abrahim L: Efficient functioning of plant promoters and polyadenylated sites in *Xenopus oocytes*. Nucl Acids Res 1989; 17: 7891–7904.

[38] Maiti I B, Richins R D, Shepherd R J: Gene expression regulated by gene VI of caulimovirus: transactivation of downstream genes of transcripts by gene VI of peanut chlorotic streak virus in transgenic tobacco. Virus Res 1998; 57:113–124.

[39] Sanger F, Nicklen S, Coulson A R: DNA sequencing with chain terminator inhibitor. Proc. Natl Acad Sci USA 1977; 74: 5463–5467.

[40] Schardl C L, Byrd A D, Benzion G, Altschuler M A, Hildebrand D F, Hunt A G: Design and construction of a versatile system for the expression of foreign genes in plants. Gene 1987; 61:1–11.

[41] Maiti I B, Murphy J F, Shaw J G, Hunt, A G: Plants that express a poty virus proteinase genes are resistant to virus infection. Proc Natl Acad Sci USA 1993; 90: 6110–6114.

[42] Jefferson R A, Kavanagh T A, Bevan M W: GUSfusion:-glucurodinase as a sensitive and versatile gene fusion marker in higher plants. EMBO J 1987; 6: 3901–3907.

[43] Bradford M M: A rapid and sensitive method for quantification of microgram quantities of protein utilizing the principle of protein dye-binding. Anal Biochem 1976; 72: 248–254.

[44] Chomczynski P, Sacchi N: Single-step method of RNA isolation by acid guanidium thiocyanate-phenolchloroform extraction. Anal Biochem 1987; 162: 156–159.

[45] Sambrook J, Fritsch E F, Maniatis T: Molecular Cloning: A Laboratory Manual, 1989, 2nd ed., Cold Spring Harbor Laboratory Press, Cold Spring Harbor, N.Y.,

[46] Guiley H, Dudley R K, Jonard G, Balasze E, Richards K E: Transcription of cauliflower mosaic virus DNA: detection of promoter sequence and characterization of transcripts. Cell 1982; 30: 763–773.

[47] Sanfacon H: Analysis of figwort mosaic virus (plant pararetrovirus) polyadenylation signal. Virology 1994; 198: 39–49.

We claim:

1. An isolated DNA molecule comprising a *mirabilis mosaic* virus (MMV) subgenomic transcript (Sgt) promoter comprising the nucleotide sequence of SEQ ID NO: 1 or SEQ ID NO: 12 or a fragment of SEQ ID NO: 1 or SEQ ID NO:12 having at least 32% MMV Sgt promoter activity.

2. An isolated DNA molecule comprising a fragment of the MMV Sgt promoter, said fragment comprising SEQ ID NO:2.

3. An isolated DNA molecule comprising a fragment of the MMV Sgt promoter, said fragment comprising SEQ ID NO:9.

4. An isolated DNA molecule comprising a fragment of the MMV Sgt promoter, said fragment comprising SEQ ID NO:13.

5. An isolated DNA molecule comprising a fragment of the MMV Sgt promoter, said fragment comprising SEQ ID NO:37.

6. An isolated DNA molecule of claim 1, 2, 3, 4 or 5 further comprising a nucleotide sequence encoding a polypeptide operably linked thereto.

7. An isolated DNA molecule of claim 6 further comprising a 3' non-translated polyadenylation signal sequence operably linked to said nucleotide sequence.

8. An isolated DNA molecule of claim 6 wherein the nucleotide sequence encoding a polypeptide is in antisense orientation relative to the promoter or promoter fragment.

9. An isolated DNA molecule of claim 1 comprising a MMV 5' non-translated leader sequence operably linked thereto.

10. An isolated DNA molecule of claim 6, wherein said DNA molecule is free of nucleotide sequences encoding MMV polypeptide.

11. An isolated DNA molecule of claim 6 wherein said nucleotide sequence encodes a plant protein.

12. An isolated DNA molecule of claim 6 wherein said nucleotide sequence encodes a heterologous protein relative to the MMV Sgt promoter.

13. An intermediate plant transformation plasmid comprising a region of homology to an *Agrobacterium tumefaciens* vector capable of transferring a gene into a cell, an *Agrobacterium tumefaciens* T-DNA border region and a chimeric gene located between the T-DNA border and the region of homology, said chimeric gene comprising a MMV Sgt promoter of claim 1 operably linked to a nucleotide sequence encoding a polypeptide.

14. An intermediate plant transformation plasmid of claim 13 wherein said polypeptide is heterologous with respect to the MMV Sgt promoter.

15. An intermediate plant transformation plasmid of claim 13, further comprising a MMV leader sequence operably linked to said nucleotide sequence.

16. An intermediate plant transformation plasmid of 13, wherein said MMV Sgt promoter comprises at least one enhancer domain.

17. A plant transformation vector comprising a disarmed *Agrobacterium tumefaciens* plant tumor-inducing plasmid and a chimeric gene, said chimeric gene comprising a MMV Sgt promoter of claim 1 operably linked to a nucleotide sequence which encodes a polypeptide.

18. A plant transformation vector of claim 17 wherein said MMV Sgt promoter comprises at least one enhancer domain.

19. A plant transformation vector of claim 17 wherein said nucleotide sequence encodes a polypeptide that is heterologous relative to the MMV Sgt promoter.

20. A plant transformation vector of claim 18 wherein the MMV Sgt promoter comprises a single enhancer domain.

21. A plant transformation vector of claim 18 wherein the MMV Sgt promoter comprises two enhancer domains.

22. A transgenic plant or transgenic plant part comprising a plant transformation vector comprising a disarmed *Agrobacterium turmefaciens* plant tumor-inducing plasmid and a chimeric gene, said chimeric gene comprising a MMV Sgt promoter comprising the nucleotide sequence of SEQ ID NO: 1 or SEQ ID NO: 12 or a fragment of SEQ ID NO: 1 or SEQ ID NO: 12 having at least 32% MMV Sgt promoter activity, wherein said MMV Sgt promoter or fragment thereof is operably linked to a nucleotide sequence which encodes a polypeptide; and wherein said chimeric gene is expressed in the plant.

23. A transgenic plant or transgenic plant part of claim 22 wherein said plant transformation vector further comprises a 3' non-translated polyadenylation signal sequence operably linked to said nucleotide sequence.

24. A transgenic plant or transgenic plant part of claim 22 wherein said nucleotide sequence encodes a plant metabolic protein or a polypeptide that confers pathogen resistance to said transgenic plant.

25. A transgenic plant or transgenic plant part of claim 22 wherein said MMV Sgt promoter comprises at least one enhancer domain.

26. A transgenic plant or transgenic plant part of claim 22 wherein said plant is a tobacco plant.

27. A transgenic plant or transgenic plant part of claim 22 wherein said polypeptide confers pathogen resistance to the transgenic plant.

28. A transgenic plant part of claim 22, wherein said plant part is selected from the group consisting of a root, leaf, flower, stem, seed, petal, pollen, callus and cell.

29. A transformed plant protoplast comprising a plant transformation vector comprising a disarmed *Agrobacterium tumefaciens* plant tumor-inducing plasmid and a chimeric gene, said chimeric gene comprising a MMV Sgt promoter comprising the nucleotide sequence of SEQ ID NO: 1 or a fragment thereof having at least 32% MMV Sgt promoter activity, wherein said MMV Sgt promoter or fragment thereof is operably linked to a nucleotide sequence which encodes a polypeptide.

30. A method of making a transgenic plant comprising (1) transforming a plant cell with a chimeric gene comprising a MMV Sgt promoter comprising the nucleotide sequence of SEQ ID NO: 1 or SEQ ID NO: 12 or a fragment of SEQ ID NO: 1 or SEQ ID NO: 12 having at least 32% MMV Sgt promoter activity, wherein said MMV Sgt promoter or fragment thereof is operably linked to a nucleotide sequence which encodes a polypeptide; (2) culturing the plant cell under growing conditions to produce a regenerated plant; and (3) and expressing the chimeric gene in the regenerated plant.

31. A method of making a transgenic plant of claim 30 wherein said chimeric gene encodes a polypeptide conferring pathogen resistance to the transgenic plant.

32. A plant promoter enhancer element comprising the nucleotide sequence of SEQ ID NO: 10.

\* \* \* \* \*

SEQUENCE LISTING

<160> NUMBER OF SEQ ID NOS: 37

<210> SEQ ID NO 1
<211> LENGTH: 1024
<212> TYPE: DNA
<213> ORGANISM: Mirabilis mosaic virus (MMV)

<400> SEQUENCE: 1
gaaaaacgga aaccgttaca ggtaaagttg aagaaagatc aggtatggat ctggacgcaa     60

```
tcagatactg attacgttaa aaagataaag aaaggattaa ttaattttcc a

<210> SEQ ID NO 5
<211> LENGTH: 12
<212> TYPE: DNA
<213> ORGANISM: Artificial Sequence
<220> FEATURE:
<223> OTHER INFORMATION: Chemically synthesized forward primer

<400> SEQUENCE: 5
aattacccgg gc                                                          12

<210> SEQ ID NO 6
<211> LENGTH: 12
<212> TYPE: DNA
<213> ORGANISM: Artificial Sequence
<220> FEATURE:
<223> OTHER INFORMATION: Chemically synthesized reverse primer

<400> SEQUENCE: 6
aattgcccgg gt                                                          12

<210> SEQ ID NO 7
<211> LENGTH: 36
<212> TYPE: DNA
<213> ORGANISM: Artificial Sequence
<220> FEATURE:
<223> OTHER INFORMATION: Chemically synthesized forward primer

<400> SEQUENCE: 7
caagaattcg ttaacaagct gcagaaagga attacc                                36

<210> SEQ ID NO 8
<211> LENGTH: 27
<212> TYPE: DNA
<213> ORGANISM: Artificial Sequence
<220> FEATURE:
<223> OTHER INFORMATION: Chemically synthesized reverse primer

<400> SEQUENCE: 8
cttaagcttg cttggaggtc tgatttt                                          27

<210> SEQ ID NO 9
<211> LENGTH: 483
<212> TYPE: DNA
<213> ORGANISM: Mirabilis mosaic virus (MMV)

<400> SEQUENCE: 9
aggcccaaac cactgaaggt gaagaattaa tctgcaggta ttcttcagga acattcaaac       60
cagcagaatt gaattaccat agtaatgaga aagaattact agcggtaaaa caggtgatta      120
ctaaatttag tatttatcta accctgtttt gttttacagt caggacagat aatgtaaatc      180
ttttaaaagg atttatgaat aaaaagatta ctggtgacag taaacaggga aggctaataa      240
gatggcaaat gtggttttca cattcaccct ttaaggtgga ccactaaaaa ggagaacaaa      300
atgtgctggc tgattatctc accagagaat tacccgggca attccacaat ggaaacgtca      360
tccatgacga ctaaacctgc cattttcgg ctataaaaac tgggttttc caaatgaaaa       420 ttccacacaa aacacatcct tttttcaaag gggggaatt aaatcaaaaa caggaaaaac      480
aaa                                                                   483

<210> SEQ ID NO 10
<211> LENGTH: 50
<212> TYPE: DNA
<213> ORGANISM: Mirabilis mosaic virus (MMV)

```
<400> SEQUENCE: 10
acattcaaac cagcagaatt gaattaccat agtaatgaga aagaattact                50

<210> SEQ ID NO 11
<211> LENGTH: 12
<212> TYPE: DNA
<213> ORGANISM: Artificial Sequence
<220> FEATURE:
<223> OTHER INFORMATION: Chemically synthesized restriction enzyme site

<400> SEQUENCE: 11
aattacccgg gc                                                         12

<210> SEQ ID NO 12
<211> LENGTH: 1012
<212> TYPE: DNA
<213> ORGANISM: Mirabilis mosaic virus (MMV)

<400> SEQUENCE: 12
gaaaaacgga aaccgttaca ggtaaagttg aagaaagatc aggtatggat ctggacgcaa     60
tcagatactg attacgttaa aaagataaag aaaggattaa ttaattttcc aaaactttat    120
ctaccaaaga aagaagacag tttaattatt gaaactgatg cttctgatca cttttggggt    180
ggagtcctta aggcccaaac cactgaaggt gaagaattaa tctgcaggta ttcttcagga    240
acattcaaac cagcagaatt gaattaccat agtaatgaga aagaattact agcggtaaaa    300
caggtgatta ctaaatttag tatttatcta acccctgttt gttttacagt caggacagat    360
aatgtaaatc ttttaaaagg atttatgaat aaaaagatta ctggtgacag taaacaggga    420
aggctaataa gatggcaaat gtggttttca cattacacct ttaaggtgga ccacctaaaa    480
ggagaacaaa atgtgctggc tgattatctc accagagaat tccacaatgg aaacgtcatc    540
catgacgact aaacctgcca ttttttcggct ataaaaactg gttttttcca atgaaaaatt    600
ccacacaaaa cacatccttt tttcaaaggg ggggaattaa atcaaaaaca ggaaaaacaa    660
aaaccagtaa tggaaaaaga gcttcaggct ctaaggatca agaaaagat cctcttggta     720 gaactcgatt ctatcagaaa acaaatcagc atttacgctg aactaactgg aagtttagac    780
caggaaggct ctgcctcaca ctctaaacct agtccacagc aaacggctga tggtaaagac    840
ggctcaaatc cgttaaaccc tgatgctttg ggaaaaagca taacggagaa cttggttcca    900
agtcctgaga aggatgaatc caagaaagtt gtcagtttac gaaaaactga aagtgggttg    960
tatatcccca cgactagtcc ggttgcaaac ggctccggta aagacacaac aa           1012

<210> SEQ ID NO 13
<211> LENGTH: 321
<212> TYPE: DNA
<213> ORGANISM: Mirabilis mosaic virus (MMV)

<400> SEQUENCE: 13
gttttacagt caggacagat aatgtaaatc ttttaaaagg atttatgaat aaaaagatta     60
ctggtgacag taaacaggga aggctaataa gatggcaaat gtggttttca cattacacct    120
ttaaggtgga ccacctaaaa ggagaacaaa atgtgctggc tgattatctc accagagaat    180
tccacaatgg aaacgtcatc catgacgact aaacctgcca ttttttcggct ataaaaactg    240 ggttttttcca atgaaaaatt ccacacaaaa cacatccttt tttcaaaggg ggggaattaa    300
atcaaaaaca ggaaaaacaa a                                              321
```

<210> SEQ ID NO 14
<211> LENGTH: 673
<212> TYPE: DNA
<213> ORGANISM: Mirabilis mosaic virus (MMV)

<400> SEQUENCE: 14

| gaaaaacgga aaccgttaca ggtaaagttg aagaaagatc aggtatggat ctggacgcaa | 60 |
| tcagatactg attacgttaa aaagataaag aaaggattaa ttaattttcc aaaactttat | 120 |
| ctaccaaaga aagaagacag tttaattatt gaaactgatg cttctgatca cttttggggt | 180 |
| ggagtcctta aggcccaaac cactgaaggt gaagaattaa tctgcaggta ttcttcagga | 240 |
| acattcaaac cagcagaatt gaattaccat agtaatgaga aagaattact agcggtaaaa | 300 |
| caggtgatta ctaaatttag tatttatcta accctgtttt gttttacagt caggacagat | 360 |
| aatgtaaatc ttttaaaagg atttatgaat aaaaagatta ctggtgacag taaacaggga | 420 |
| aggctaataa gatggcaaat gtggttttca cattcaccct taaggtgga ccacctaaaa | 480 |
| ggagaacaaa atgtgctggc tgattatctc accagagaat tacccgggca attccacaat | 540 |
| ggaaacgtca tccatgacga ctaaacctgc cattttttcgg ctataaaaac tgggttttc | 600 |
| caaatgaaaa ttccacacaa aacacatcct tttttcaaag ggggggaatt aaatcaaaaa | 660 |
| caggaaaaac aaa | 673 |

<210> SEQ ID NO 15
<211> LENGTH: 633
<212> TYPE: DNA
<213> ORGANISM: Mirabilis mosaic virus (MMV)

<400> SEQUENCE: 15

| aggtatggat ctggacgcaa tcagatactg attacgttaa aaagataaag aaaggattaa | 60 |
| ttaattttcc aaaactttat ctaccaaaga aagaagacag tttaattatt gaaactgatg | 120 |
| cttctgatca cttttggggt ggagtcctta aggcccaaac cactgaaggt gaagaattaa | 180 |
| tctgcaggta ttcttcagga acattcaaac cagcagaatt gaattaccat agtaatgaga | 240 |
| aagaattact agcggtaaaa caggtgatta ctaaatttag tatttatcta accctgttt | 300 |
| gttttacagt caggacagat aatgtaaatc ttttaaaagg atttatgaat aaaaagatta | 360 |
| ctggtgacag taaacaggga aggctaataa gatggcaaat gtggttttca cattcaccct | 420 |
| taaggtgga ccacctaaaa ggagaacaaa atgtgctggc tgattatctc accagagaat | 480 |
| tacccgggca attccacaat ggaaacgtca tccatgacga ctaaacctgc cattttttcgg | 540 |
| ctataaaaac tgggttttc caaatgaaaa ttccacacaa aacacatcct tttttcaaag | 600 |
| ggggggaatt aaatcaaaaa caggaaaaac aaa | 633 |

<210> SEQ ID NO 16
<211> LENGTH: 583
<212> TYPE: DNA
<213> ORGANISM: Mirabilis mosaic virus (MMV)

<400> SEQUENCE: 16

| aaaggattaa ttaattttcc aaaactttat ctaccaaaga aagaagacag tttaattatt | 60 |
| gaaactgatg cttctgatca cttttggggt ggagtcctta aggcccaaac cactgaaggt | 120 |
| gaagaattaa tctgcaggta ttcttcagga acattcaaac cagcagaatt gaattaccat | 180 |
| agtaatgaga aagaattact agcggtaaaa caggtgatta ctaaatttag tatttatcta | 240 |
| accctgtttt gttttacagt caggacagat aatgtaaatc ttttaaaagg atttatgaat | 300 |

| | |
|---|---|
| aaaaagatta ctggtgacag taaacaggga aggctaataa gatggcaaat gtggttttca | 360 |
| cattcaccct ttaaggtgga ccacctaaaa ggagaacaaa atgtgctggc tgattatctc | 420 |
| accagagaat tacccgggca attccacaat ggaaacgtca tccatgacga ctaaacctgc | 480 |
| cattttccgg ctataaaaac tgggttttttc caaatgaaaa ttccacacaa aacacatcct | 540 |
| tttttcaaag gggggaatt aaatcaaaaa caggaaaaac aaa | 583 |

<210> SEQ ID NO 17
<211> LENGTH: 533
<212> TYPE: DNA
<213> ORGANISM: Mirabilis mosaic virus (MMV)

<400> SEQUENCE: 17

| | |
|---|---|
| tttaattatt gaaactgatg cttctgatca cttttggggt ggagtcctta aggcccaaac | 60 |
| cactgaaggt gaagaattaa tctgcaggta ttcttcagga acattcaaac cagcagaatt | 120 |
| gaattaccat agtaatgaga aagaattact agcggtaaaa caggtgatta ctaaatttag | 180 |
| tatttatcta acccctgttt gttttacagt caggacagat aatgtaaatc ttttaaaagg | 240 |
| atttatgaat aaaagatta ctggtgacag taaacaggga aggctaataa gatggcaaat | 300 |
| gtggttttca cattcaccct ttaaggtgga ccacctaaaa ggagaacaaa atgtgctggc | 360 |
| tgattatctc accagagaat tacccgggca attccacaat ggaaacgtca tccatgacga | 420 |
| ctaaacctgc cattttccgg ctataaaaac tgggttttttc caaatgaaaa ttccacacaa | 480 |
| aacacatcct tttttcaaag gggggaatt aaatcaaaaa caggaaaaac aaa | 533 |

<210> SEQ ID NO 18
<211> LENGTH: 433
<212> TYPE: DNA
<213> ORGANISM: Mirabilis mosaic virus (MMV)

<400> SEQUENCE: 18

| | |
|---|---|
| acattcaaac cagcagaatt gaattaccat agtaatgaga aagaattact agcggtaaaa | 60 |
| caggtgatta ctaaatttag tatttatcta acccctgttt gttttacagt caggacagat | 120 |
| aatgtaaatc ttttaaaagg atttatgaat aaaagatta ctggtgacag taaacaggga | 180 |
| aggctaataa gatggcaaat gtggttttca cattcaccct ttaaggtgga ccacctaaaa | 240 |
| ggagaacaaa atgtgctggc tgattatctc accagagaat tacccgggca attccacaat | 300 |
| ggaaacgtca tccatgacga ctaaacctgc cattttccgg ctataaaaac tgggttttttc | 360 |
| caaatgaaaa ttccacacaa aacacatcct tttttcaaag gggggaatt aaatcaaaaa | 420 |
| caggaaaaac aaa | 433 |

<210> SEQ ID NO 19
<211> LENGTH: 383
<212> TYPE: DNA
<213> ORGANISM: Mirabilis mosaic virus (MMV)

<400> SEQUENCE: 19

| | |
|---|---|
| agcggtaaaa caggtgatta ctaaatttag tatttatcta acccctgttt gttttacagt | 60 |
| caggacagat aatgtaaatc ttttaaaagg atttatgaat aaaagatta ctggtgacag | 120 |
| taaacaggga aggctaataa gatggcaaat gtggttttca cattcaccct ttaaggtgga | 180 |
| ccacctaaaa ggagaacaaa atgtgctggc tgattatctc accagagaat tacccgggca | 240 |
| attccacaat ggaaacgtca tccatgacga ctaaacctgc cattttccgg ctataaaaac | 300 |
| tgggttttttc caaatgaaaa ttccacacaa aacacatcct tttttcaaag gggggaatt | 360 |

-continued

```
aaatcaaaaa caggaaaaac aaa                                              383

<210> SEQ ID NO 20
<211> LENGTH: 283
<212> TYPE: DNA
<213> ORGANISM: Mirabilis mosaic virus (MMV)

<400> SEQUENCE: 20
aaaaagatta ctggtgacag taaacaggga aggctaataa gatggcaaat gtggttttca       60
cattacacct ttaaggtgga ccacctaaaa ggagaacaaa atgtgctggc tgattatctc      120
accagagaat tacccgggca attccacaat ggaaacgtca tccatgacga ctaaacctgc      180
catttttcgg ctataaaaac tgggtttttc caaatgaaaa ttccacacaa aacacatcct      240
tttttcaaag ggggggaatt aaatcaaaaa caggaaaaac aaa                        283

<210> SEQ ID NO 21
<211> LENGTH: 233
<212> TYPE: DNA
<213> ORGANISM: Mirabilis mosaic virus (MMV)

<400> SEQUENCE: 21
gtggttttca cattacacct ttaaggtgga ccacctaaaa ggagaacaaa atgtgctggc       60
tgattatctc accagagaat tacccgggca attccacaat ggaaacgtca tccatgacga      120
ctaaacctgc catttttcgg ctataaaaac tgggtttttc caaatgaaaa ttccacacaa      180
aacacatcct tttttcaaag ggggggaatt aaatcaaaaa caggaaaaac aaa             233

<210> SEQ ID NO 22
<211> LENGTH: 183
<212> TYPE: DNA
<213> ORGANISM: Mirabilis mosaic virus (MMV)

<400> SEQUENCE: 22
atgtgctggc tgattatctc accagagaat tacccgggca attccacaat ggaaacgtca       60
tccatgacga ctaaacctgc catttttcgg ctataaaaac tgggtttttc caaatgaaaa      120
ttccacacaa aacacatcct tttttcaaag ggggggaatt aaatcaaaaa caggaaaaac      180
aaa                                                                    183

<210> SEQ ID NO 23
<211> LENGTH: 144
<212> TYPE: DNA
<213> ORGANISM: Mirabilis mosaic virus (MMV)

<400> SEQUENCE: 23
aattccacaa tggaaacgtc atccatgacg actaaacctg ccatttttcg gctataaaaa       60
ctgggttttt ccaaatgaaa attccacaca aaacacatcc ttttttcaaa gggggggaat      120
taaatcaaaa acaggaaaaa caaa                                             144

<210> SEQ ID NO 24
<211> LENGTH: 121
<212> TYPE: DNA
<213> ORGANISM: Mirabilis mosaic virus (MMV)

<400> SEQUENCE: 24
catgacgact aaacctgcca tttttcggct ataaaaactg ggtttttcca aatgaaaatt       60
ccacacaaaa cacatccttt tttcaaaggg ggggaattaa atcaaaaaca ggaaaaacaa      120

—continued a                                                                121

<210> SEQ ID NO 25
<211> LENGTH: 101
<212> TYPE: DNA
<213> ORGANISM: Mirabilis mosaic virus (MMV)

<400> SEQUENCE: 25
tttttcggct ataaaaactg ggttttccca aatgaaaatt ccacacaaaa cacatccttt      60
tttcaaaggg ggggaattaa atcaaaaaca ggaaaaacaa a                        101

<210> SEQ ID NO 26
<211> LENGTH: 71
<212> TYPE: DNA
<213> ORGANISM: Mirabilis mosaic virus (MMV)

<400> SEQUENCE: 26
aatgaaaatt ccacacaaaa cacatccttt tttcaaaggg ggggaattaa atcaaaaaca      60
ggaaaaacaa a                                                         71

<210> SEQ ID NO 27
<211> LENGTH: 383
<212> TYPE: DNA
<213> ORGANISM: Mirabilis mosaic virus (MMV)

<400> SEQUENCE: 27
aggcccaaac cactgaaggt gaagaattaa tctgcaggta ttcttcagga acattcaaac      60
cagcagaatt gaattaccat agtaatgaga aagaattact agcggtaaaa caggtgatta     120
ctaaatttag tatttatcta acccctgttt gttttacagt caggacagat aatgtaaatc     180
ttttaaaagg atttatgaat aaaaagatta ctggtgacag taaacaggga aggctaataa     240
gatggcaaat gtggttttca cattcaccct ttaaggtgga ccactaaaaa ggagaacaaa     300
atgtgctggc tgattatctc accagagaat tacccgggca attccacaat ggaaacgtca     360
tccatgacga ctaaacctgc cat                                            383

<210> SEQ ID NO 28
<211> LENGTH: 438
<212> TYPE: DNA
<213> ORGANISM: Mirabilis mosaic virus (MMV)

<400> SEQUENCE: 28
aggcccaaac cactgaaggt gaagaattaa tctgcaggta ttcttcagga acattcaaac      60
cagcagaatt gaattaccat agtaatgaga aagaattact agcggtaaaa caggtgatta     120
ctaaatttag tatttatcta acccctgttt gttttacagt caggacagat aatgtaaatc     180
ttttaaaagg atttatgaat aaaaagatta ctggtgacag taaacaggga aggctaataa     240
gatggcaaat gtggttttca cattcaccct ttaaggtgga ccactaaaaa ggagaacaaa     300
atgtgctggc tgattatctc accagagaat tacccgggca attccacaat ggaaacgtca     360
tccatgacga ctaaacctgc cattttttcgg ctataaaaac tgggttttc caaatgaaaa     420 ttccacacaa aacacatc                                                  438

<210> SEQ ID NO 29
<211> LENGTH: 356
<212> TYPE: DNA
<213> ORGANISM: Mirabilis mosaic virus (MMV)

<400> SEQUENCE: 29

```
gttttacagt caggacagat aatgtaaatc ttttaaaagg atttatgaat aaaaagatta      60
ctggtgacag taaacaggga aggctaataa gatggcaaat gtggttttca cattacacct     120
ttaaggtgga ccacctaaaa ggagaacaaa atgtgctggc tgattatctc accagagaat     180
tacccgggca attccacaat ggaaacgtca tccatgacga ctaaacctgc cattttcgg     240 ctataaaaac tgggttttc caaatgaaaa ttccacacaa aacacatcct tttttcaaag     300
ggggggaatt aaatcaaaaa caggaaaaac aaaaaccagt aatggaaaaa gagctt        356

<210> SEQ ID NO 30
<211> LENGTH: 383
<212> TYPE: DNA
<213> ORGANISM: Mirabilis mosaic virus (MMV)

<400> SEQUENCE: 30
gttttacagt caggacagat aatgtaaatc ttttaaaagg atttatgaat aaaaagatta      60
ctggtgacag taaacaggga aggctaataa gatggcaaat gtggttttca cattacacct     120
ttaaggtgga ccacctaaaa ggagaacaaa atgtgctggc tgattatctc accagagaat     180
tacccgggca attccacaat ggaaacgtca tccatgacga ctaaacctgc cattttcgg     240 ctataaaaac tgggttttc caaatgaaaa ttccacacaa aacacatcct tttttcaaag     300
ggggggaatt aaatcaaaaa caggaaaaac aaaaaccagt aatggaaaaa gagcttcagg    360
ctctaaggat caaagaaaag atc                                             383

<210> SEQ ID NO 31
<211> LENGTH: 433
<212> TYPE: DNA
<213> ORGANISM: Mirabilis mosaic virus (MMV)

<400> SEQUENCE: 31
gttttacagt caggacagat aatgtaaatc ttttaaaagg atttatgaat aaaaagatta      60
ctggtgacag taaacaggga aggctaataa gatggcaaat gtggttttca cattacacct     120
ttaaggtgga ccacctaaaa ggagaacaaa atgtgctggc tgattatctc accagagaat     180
tacccgggca attccacaat ggaaacgtca tccatgacga ctaaacctgc cattttcgg     240 ctataaaaac tgggttttc caaatgaaaa ttccacacaa aacacatcct tttttcaaag     300
ggggggaatt aaatcaaaaa caggaaaaac aaaaaccagt aatggaaaaa gagcttcagg    360
ctctaaggat caaagaaaag atcctcttgg tagaactcga ttctatcaga aaacaaatca    420
gcatttacgc tga                                                         433

<210> SEQ ID NO 32
<211> LENGTH: 483
<212> TYPE: DNA
<213> ORGANISM: Mirabilis mosaic virus (MMV)

<400> SEQUENCE: 32
gttttacagt caggacagat aatgtaaatc ttttaaaagg atttatgaat aaaaagatta      60
ctggtgacag taaacaggga aggctaataa gatggcaaat gtggttttca cattacacct     120
ttaaggtgga ccacctaaaa ggagaacaaa atgtgctggc tgattatctc accagagaat     180
tacccgggca attccacaat ggaaacgtca tccatgacga ctaaacctgc cattttcgg     240 ctataaaaac tgggttttc caaatgaaaa ttccacacaa aacacatcct tttttcaaag     300
ggggggaatt aaatcaaaaa caggaaaaac aaaaaccagt aatggaaaaa gagcttcagg    360
```

-continued

```
ctctaaggat caaagaaaag atcctcttgg tagaactcga ttctatcaga aaacaaatca    420
gcatttacgc tgaactaact ggaagtttag accaggaagg ctctgcctca cactctaaac    480
cta                                                                  483
```

<210> SEQ ID NO 33
<211> LENGTH: 533
<212> TYPE: DNA
<213> ORGANISM: Mirabilis mosaic virus (MMV)

<400> SEQUENCE: 33

```
gttttacagt caggacagat aatgtaaatc ttttaaaagg atttatgaat aaaaagatta     60
ctggtgacag taaacaggga aggctaataa gatggcaaat gtggttttca cattacacct    120
ttaaggtgga ccacctaaaa ggagaacaaa atgtgctggc tgattatctc accagagaat    180
tacccgggca attccacaat ggaaacgtca tccatgacga ctaaacctgc cattttttcgg   240 ctataaaaac tgggttttttc caaatgaaaa ttccacacaa aacacatcct ttttttcaaag  300 gggggggaatt aaatcaaaaa caggaaaaac aaaaaccagt aatggaaaaa gagcttcagg   360
ctctaaggat caaagaaaag atcctcttgg tagaactcga ttctatcaga aaacaaatca    420
gcatttacgc tgaactaact ggaagtttag accaggaagg ctctgcctca cactctaaac    480
ctagtccaca gcaaacggct gatggtaaag acggctcaaa tccgttaaac cct           533
```

<210> SEQ ID NO 34
<211> LENGTH: 583
<212> TYPE: DNA
<213> ORGANISM: Mirabilis mosaic virus (MMV)

<400> SEQUENCE: 34

```
gttttacagt caggacagat aatgtaaatc ttttaaaagg atttatgaat aaaaagatta     60
ctggtgacag taaacaggga aggctaataa gatggcaaat gtggttttca cattacacct    120
ttaaggtgga ccacctaaaa ggagaacaaa atgtgctggc tgattatctc accagagaat    180
tacccgggca attccacaat ggaaacgtca tccatgacga ctaaacctgc cattttttcgg   240 ctataaaaac tgggttttttc caaatgaaaa ttccacacaa aacacatcct tttttcaaag   300 gggggggaatt aaatcaaaaa caggaaaaac aaaaaccagt aatggaaaaa gagcttcagg   360
ctctaaggat caaagaaaag atcctcttgg tagaactcga ttctatcaga aaacaaatca    420
gcatttacgc tgaactaact ggaagtttag accaggaagg ctctgcctca cactctaaac    480
ctagtccaca gcaaacggct gatggtaaag acggctcaaa tccgttaaac cctgatgctt    540
tgggaaaaag cataacggag aacttggttc caagtcctga gaa                      583
```

<210> SEQ ID NO 35
<211> LENGTH: 633
<212> TYPE: DNA
<213> ORGANISM: Mirabilis mosaic virus (MMV)

<400> SEQUENCE: 35

```
gttttacagt caggacagat aatgtaaatc ttttaaaagg atttatgaat aaaaagatta     60
ctggtgacag taaacaggga aggctaataa gatggcaaat gtggttttca cattacacct    120
ttaaggtgga ccacctaaaa ggagaacaaa atgtgctggc tgattatctc accagagaat    180
tacccgggca attccacaat ggaaacgtca tccatgacga ctaaacctgc cattttttcgg   240 ctataaaaac tgggttttttc caaatgaaaa ttccacacaa aacacatcct tttttcaaag   300 gggggggaatt aaatcaaaaa caggaaaaac aaaaaccagt aatggaaaaa gagcttcagg   360
```

-continued

```
ctctaaggat caaagaaaag atcctcttgg tagaactcga ttctatcaga aaacaaatca      420
gcatttacgc tgaactaact ggaagtttag accaggaagg ctctgcctca cactctaaac      480
ctagtccaca gcaaacggct gatggtaaag acggctcaaa tccgttaaac cctgatgctt      540
tgggaaaaag cataacggag aacttggttc caagtcctga gaaggatgaa tccaagaaag      600
ttgtcagttt acgaaaaact gaaagtgggt tgt                                   633

<210> SEQ ID NO 36
<211> LENGTH: 683
<212> TYPE: DNA
<213> ORGANISM: Mirabilis mosaic virus (MMV)

<400> SEQUENCE: 36
gttttacagt caggacagat aatgtaaatc ttttaaaagg atttatgaat aaaaagatta       60
ctggtgacag taaacaggga aggctaataa gatggcaaat gtggttttca cattacacct      120
ttaaggtgga ccacctaaaa ggagaacaaa atgtgctggc tgattatctc accagagaat      180
tacccgggca attccacaat ggaaacgtca tccatgacga ctaaacctgc catttttcgg      240
ctataaaaac tgggtttttc caaatgaaaa ttccacacaa aacacatcct tttttcaaag      300 gggggggaatt aaatcaaaaa caggaaaaac aaaaaccagt aatggaaaaa gagcttcagg     360
ctctaaggat caaagaaaag atcctcttgg tagaactcga ttctatcaga aaacaaatca     420
gcatttacgc tgaactaact ggaagtttag accaggaagg ctctgcctca cactctaaac     480
ctagtccaca gcaaacggct gatggtaaag acggctcaaa tccgttaaac cctgatgctt     540
tgggaaaaag cataacggag aacttggttc caagtcctga gaaggatgaa tccaagaaag     600
ttgtcagttt acgaaaaact gaaagtgggt tgtatatccc cacgactagt ccggttgcaa     660
acggctccgg taaagacaca aca                                             683

<210> SEQ ID NO 37
<211> LENGTH: 471
<212> TYPE: DNA
<213> ORGANISM: Mirabilis mosaic virus (MMV)

<400> SEQUENCE: 37
aggcccaaac cactgaaggt gaagaattaa tctgcaggta ttcttcagga acattcaaac       60
cagcagaatt gaattaccat agtaatgaga aagaattact agcggtaaaa caggtgatta      120
ctaaatttag tatttatcta acccctgttt gttttacagt caggacagat aatgtaaatc      180
ttttaaaagg atttatgaat aaaaagatta ctggtgacag taaacaggga aggctaataa      240
gatggcaaat gtggttttca cattacacct ttaaggtgga ccacctaaaa ggagaacaaa      300
atgtgctggc tgattatctc accagagaat tccacaatgg aaacgtcatc catgacgact      360
aaacctgcca ttttcggct ataaaaactg ggttttcca aatgaaaatt ccacacaaaa       420
cacatccttt tttcaaaggg ggggaattaa atcaaaaaca ggaaaaacaa a              471
```